US010976660B2

(12) United States Patent
Qian

(10) Patent No.: US 10,976,660 B2
(45) Date of Patent: Apr. 13, 2021

(54) FLUORENE PHOTOINITIATOR, PREPARATION METHOD THEREFOR, PHOTOCURABLE COMPOSITION HAVING SAME, AND USE OF SAME IN PHOTOCURING FIELD

(71) Applicants: Changzhou Tronly Advanced Electronic Materials Co., Ltd., Changzhou (CN); Changzhou Tronly New Electronic Materials Co., Ltd., Changzhou (CN)

(72) Inventor: Xiaochun Qian, Changzhou (CN)

(73) Assignee: CHANGZHOU TRONLY ADVANCED ELECTRONIC MATERIALS CO, LTD., Jiangsu (CN)

(*) Notice: Subject to any disclaimer, the term of this patent is extended or adjusted under 35 U.S.C. 154(b) by 153 days.

(21) Appl. No.: 16/259,779

(22) Filed: Jan. 28, 2019

(65) Prior Publication Data
US 2019/0155153 A1  May 23, 2019

Related U.S. Application Data

(63) Continuation of application No. PCT/CN2017/099294, filed on Aug. 28, 2017.

(30) Foreign Application Priority Data

Sep. 13, 2016  (CN) .................. 201610821992.3
Jun. 28, 2017  (CN) .................. 201710530354.0

(51) Int. Cl.
C07C 49/21       (2006.01)
C08F 2/50        (2006.01)
G03F 7/031       (2006.01)
C07C 225/22      (2006.01)
C07D 295/104     (2006.01)
C07C 45/63       (2006.01)
C07C 323/22      (2006.01)
(Continued)

(52) U.S. Cl.
CPC .............. G03F 7/031 (2013.01); C07C 45/46 (2013.01); C07C 45/63 (2013.01); C07C 45/64 (2013.01); C07C 49/215 (2013.01); C07C 49/84 (2013.01); C07C 67/03 (2013.01); C07C 67/343 (2013.01); C07C 69/738 (2013.01); C07C 225/22 (2013.01); C07C 323/22 (2013.01); C07D 295/104 (2013.01); C08F 2/46 (2013.01); C08F 2/50 (2013.01); C08F 290/067 (2013.01); C09D 11/101 (2013.01); C09D 11/322 (2013.01); C09D 11/38 (2013.01); C09D 133/08 (2013.01); C09D 175/16 (2013.01); C07C 2601/08 (2017.05);
C07C 2603/18 (2017.05); C08F 20/00 (2013.01); C09D 167/00 (2013.01); C09D 175/04 (2013.01)

(58) Field of Classification Search
CPC ............ C07C 2603/18; C07C 2601/08; C07C 323/22; C07C 225/22; C07C 69/738; C07C 67/03; C07C 67/343; C07C 49/84; C07C 49/215; C07C 45/64; C07C 45/63; C07C 25/46; G03F 7/031; C09D 175/16; C09D 175/04; C09D 167/00; C09D 133/08; C09D 11/38; C09D 11/322; C09D 11/101; C08F 290/067; C08F 290/061; C08F 20/00; C08F 2/50; C08F 2/46; C08D 295/112; C08D 295/104
See application file for complete search history.

(56) References Cited

U.S. PATENT DOCUMENTS 4,374,984 A    2/1983  Eichler et al.
4,533,670 A    8/1985  Robertson
(Continued)

FOREIGN PATENT DOCUMENTS

CN    101724099    6/2010
CN    102267837    12/2011
(Continued)

OTHER PUBLICATIONS

Minabe et al. Syntheses and Some Properties of 9,2':7',9"-, 9,2':9',9"-, and 9,4':9',9"-Terfluorene. Bulletin of the Chemical Society of Japan 1978 51:11, 3373-3376 (Year: 1978).*
PubChem Bethesda (MD): National Library of Medicine (US), National Center for Biotechnology Information; 2004-. PubChem Compound Summary for CID 97070, Methanone, 9H-fluoren-2-ylphenyl-; [cited Oct. 8, 2020]. Available from: https://pubchem.ncbi.nlm.nih.gov/compound/Methanone_-9H-fluoren-2-yl. (Year: 2004).*
Bolton et al. The stability of Carbonium ions. Journal of the Chemical Society. (1964). pp. 1464-1466. (Year: 1964).*
(Continued)

Primary Examiner — Sanza L. McClendon
(74) Attorney, Agent, or Firm — Pillsbury Winthrop Shaw Pittman LLP

(57) ABSTRACT

A fluorene-based photoinitiator, a preparation method thereof, a photocurable composition having the same, and use thereof in the field of photocuring are disclosed. In some embodiments, the fluorene-based photoinitiator has a structure represented by Formula I, wherein X is -A-(X')$_n$, wherein A is selected from a heteroatom which is selected from O, N, or S, X' is selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group or one or more of carbon atoms in X' are substituted with a heteroatom, and n is 1 or 2; and $R_4$ is a hydroxy group or a N-morpholinyl group. In some embodiments, the fluorene-based photoinitiator comprises a structure represented by Formula II.

18 Claims, No Drawings

US 10,976,660 B2
Page 2

(51) Int. Cl.

| | | |
|---|---|---|
| C07C 69/738 | (2006.01) | |
| C09D 11/101 | (2014.01) | |
| C07C 45/46 | (2006.01) | |
| C07C 45/64 | (2006.01) | |
| C07C 67/03 | (2006.01) | |
| C09D 175/16 | (2006.01) | |
| C07C 49/84 | (2006.01) | |
| C08F 290/06 | (2006.01) | |
| C07C 67/343 | (2006.01) | |
| C07C 49/215 | (2006.01) | |
| C08F 2/46 | (2006.01) | |
| C09D 11/322 | (2014.01) | |
| C09D 11/38 | (2014.01) | |
| C09D 133/08 | (2006.01) | |
| C08F 20/00 | (2006.01) | |
| C09D 167/00 | (2006.01) | |
| C09D 175/04 | (2006.01) | |

(56) References Cited

U.S. PATENT DOCUMENTS

| | | | |
|---|---|---|---|
| 4,666,624 | A | 5/1987 | Messer |
| 4,950,581 | A | 8/1990 | Koike et al. |
| 5,077,402 | A | 12/1991 | Desobry et al. |
| 5,527,925 | A | 6/1996 | Chabrecek et al. |
| 5,612,389 | A | 3/1997 | Chabrecek et al. |
| 5,612,391 | A | 3/1997 | Chabrecek et al. |
| 5,621,018 | A | 4/1997 | Chabrecek et al. |
| 6,087,412 | A | 7/2000 | Chabrecek et al. |
| 6,099,122 | A | 8/2000 | Chabrecek et al. |
| 6,204,306 | B1 | 3/2001 | Chabrecek et al. |
| 6,492,514 | B1 | 12/2002 | Meneguzzo et al. |
| 9,316,906 | B2 | 4/2016 | Shin et al. |
| 9,684,238 | B2 | 6/2017 | Harihara et al. |
| 9,873,663 | B2 | 1/2018 | Oh et al. |
| 2005/0266341 | A1 | 12/2005 | Kim |
| 2015/0111152 | A1 | 4/2015 | Shin et al. |
| 2015/0259321 | A1 | 9/2015 | Harihara et al. |
| 2016/0046551 | A1 | 2/2016 | Shiota et al. |
| 2017/0160636 | A1 | 6/2017 | Tadokoro et al. |
| 2018/0050973 | A1 | 2/2018 | Shiota et al. |
| 2019/0155153 | A1 | 5/2019 | Qian |
| 2020/0002544 | A1 | 1/2020 | Changzhou Tronly Advanced Elec Mat Coltd et al. |

FOREIGN PATENT DOCUMENTS

| | | | | |
|---|---|---|---|---|
| CN | 104661997 | | 5/2015 | |
| CN | 104661997 | A | 5/2015 | |
| CN | 104684888 | | 6/2015 | |
| CN | 104684888 | A | 6/2015 | |
| CN | 104892512 | A | 9/2015 | |
| CN | 105916837 | | 8/2016 | |
| CN | 106883114 | A | 6/2017 | |
| EP | 2913323 | A1 | 9/2015 | |
| EP | 3165965 | A1 | 5/2017 | |
| EP | 3392232 | | 10/2018 | |
| GB | 1189514 | A | 4/1970 | |
| JP | 200134812 | | 12/2001 | |
| JP | 2009019142 | | 1/2009 | |
| JP | H212009019142 | A | 1/2009 | |
| JP | 2009029859 | | 2/2009 | |
| JP | H212009029859 | A | 2/2009 | |
| JP | 2010024291 | | 2/2010 | |
| JP | 2017533288 | | 11/2017 | |
| JP | 2019528331 | | 10/2019 | |
| JP | 6725663 | | 6/2020 | |
| KR | 1020140076607 | | 6/2014 | |
| KR | 20140144809 | | 12/2014 | |
| KR | 20140144809 | A * | 12/2014 | |
| KR | 1020140144809 | | 12/2014 | |
| KR | 1020150040372 | | 4/2015 | |
| KR | 101567837 | B1 | 11/2015 | |
| KR | 1020170032372 | | 3/2017 | |
| WO | 2005014515 | A2 | 2/2005 | |
| WO | 2013165207 | | 11/2013 | |
| WO | 2014050738 | | 4/2014 | |
| WO | 2014050738 | A1 | 4/2014 | |
| WO | WO-2015084114 | A1 * | 6/2015 | ......... H01L 51/0059 |
| WO | 2015108386 | | 7/2015 | |
| WO | 2015108386 | A1 | 7/2015 | |
| WO | WO 2015108386 | A1 | 7/2015 | |
| WO | 2016010036 | | 1/2016 | |
| WO | 2016010036 | A1 | 1/2016 | |
| WO | WO 2016010036 | A1 | 1/2016 | |
| WO | WO-2016078603 | A1 * | 5/2016 | ........... G01N 33/582 |
| WO | 2017101553 | | 6/2017 | |
| WO | 2018049976 | | 3/2018 | |

OTHER PUBLICATIONS

Bachmann, et al., "The Rates of Dissociation of Pentaarylethanes", Contribution from the Chemistry Laboratory of the University of Michigan, Journal of Organic Chemistry, vol. 8(4), 1943, pp. 320-330.

Xuong, et al., "Potential Chemical Pituitary Inhibitors of the Polyarylethylene Series", Department of Organic Chemistry, Radium Institute, University of Paris, Journal of the Chemical Society, 1952, pp. 3741-3744.

Chardonnens, et al., "Fluorenacenes and Fluorenaphenes, Synthesis of a Series of Indenofluorenes XVII. Methyl Derivatives of cis-Fluorenacene, trans-Fluorenacene and trans-Fluorenaphene", Helvetica Chimica Acta. vol. 57(3), 1974, pp. 585-599.

Horhold, et al., "Synthesis and Photoconductivity of Poly (2,7-fluorenylene-1,2-diphenylvinylen)", Studies on Poly(arylenevinylenes), Acta Polymerica, vol. 37(6), 1986, pp. 369-375.

Park, et al., "Design and Synthesis of New Fluorene-Based Blue Light Emitting Polymer Containing Electron Donating Alkoxy Groups and Electron Withdrawing Oxadiazole", Macromolecular Research, vol. 15(3), 2007, pp. 216-220.

International Search Report and Written Opinion dated Nov. 16, 2017 in connection with International application No. PCT/CN2017/099294.

Office Action dated Aug. 22, 2019 issued in connection with Chinese App. No. 201710530354.0.

Office Action dated Jan. 28, 2020 issued in connection with Japanese App. No. 2019-501481.

Extended European Search Report dated Apr. 1, 2020 issued in connection with European App. No. 17850178.9.

Office Action dated Mar. 27, 2020 issued in connection with Chinese App. No. 201610821992.3.

Cha et al, KR 1020140144809 Machine Translation (Dec. 22, 2014).

Cheng et al, WO 2017101553 Machine Translation (Jun. 22, 2017).

Database Registry[online]. STN International, Columbus, Ohio, USA, Oct. 27, 2016 (Oct. 27, 2016), CAS RN 2020359-04-8.

International Search Report as issued in International Patent Application No, PCT/CN2018/076209, dated May 10, 2018.

Written Opinion of the International Searching Authority as issued in international Patent Aoolication No. PCT/ CN2013/076209, dated May 10, 2018.

Office Action dated Aug. 6, 2020, issued in JP Application No. 2019-544745, with English translation.

Morand, Peter et al., "The Effect of Substituted Carboxylic Acids on Hepatic Cholesterogenesis", Journal of Medicinal Chemistry, US American Chemical Society, vol. 7. No. 7, pp. 504-508 (1964).

International Search Report dated Dec. 30, 2016, issued in International Application No, PCT/CN20161100601, with English translation.

Written Opinion dated Dec. 30, 2016, issued in International Application No. PCT/CN2016/100601, with English translation.

Office Action dated May 8, 2019, issued in JP Application No. 2013-530699, with English translation Office Action dated Mar. 1, 2019, issued in JP Application No. 2013-517395, with English translation.

Office Action dated Jul. 4, 2019, issued in JP Application No. 2018-517895, with English translation.

(56) References Cited

OTHER PUBLICATIONS

Office Action dated Feb. 28, 2019, issued in CN Application No. 201510937328.0, with English translation.
Office Action dated Jun. 4, 2019, issued in CN Application No. 201610210118.6, with English translation.
Notice of Allowance dated Oct. 9, 2019, issued in CN Application No. 201510937328.0, with English translation.
Extended Search Report dated Jul. 29, 2019, issued in EP Application No. 16874613.9.
Office Action dated Nov. 21, 2019, issued in Korean application No. 10-2018-7019720, with English translation.
Office Action dated Feb. 3, 2020, issued in Chinese application No. 201610210118.6, with English translation.
Office Action dated Nov. 29, 2019, issued in Korean application No. 10-2018-7012617, with English translation.
Notice of Allowance dated Feb. 3, 2020, issued in Korean application No. 10-2018-7019720, with English translation.
Office Action dated May 27, 2020, issued in KR Application No. 10-2018-7012617, with English Translation.
Robertson, David W et al.: "Structure-Activity Relationships of (ArylalkyOimidazole Anticonvulsants: Comparison of the (Fluorenylalkyl)imidazoles with Nafimidone and Denzimol", J. Med. Chem., 29, 9, 1577-1586 (1986).
U.S. Restriction Requirement issued in corresponding U.S. Appl. No. 16/061,490, dated Nov. 18, 2020.
U.S. Office Action issued in corresponding U.S. Appl. No. 16/061,490, dated Feb. 21, 2021.

* cited by examiner

FLUORENE PHOTOINITIATOR, PREPARATION METHOD THEREFOR, PHOTOCURABLE COMPOSITION HAVING SAME, AND USE OF SAME IN PHOTOCURING FIELD

CROSS-REFERENCE TO RELATED APPLICATIONS

This application is a continuation of International Application No. PCT/CN2017/099294 having an international filing date of Aug. 28, 2017 entitled "Fluorene Photoinitiator, Preparation Method Therefore, Photocurable Composition Having Same, and Use of Same in Photocuring Field". The '294 international application claimed priority benefits from Chinese Patent Application No. 201610821992.3 filed on Sep. 13, 2016. The '294 international application also claimed priority benefits from Chinese Patent Application No. 201710530354.0 filed on Jun. 28, 2017.

The '294 international application is hereby incorporated by reference herein in its entirety.

FIELD OF THE INVENTION

This invention relates to the field of photocuring, and particularly to a fluorene-based photoinitiator, a preparation method thereof, a photocurable composition having the same, and/or uses thereof in the field of photocuring.

Conventional micromolecular photoinitiators have excellent photosensitive properties and solubility. However, they have problems, such as the easy migration of photolysis fragments, large volatility, and the like, in practical applications. Some have sought to address these deficiencies by increasing the molecular weight of the compound, but the increase of the molecular weight typically reduces the effect of photoinitiation.

Fluorene-based compounds have relatively large molecular weights, and their applications in ultraviolet photocuring are well known. Their uses as photoinitiators can overcome problems encountered by conventional micromolecular photoinitiators. However, the problem encountered by a fluorene-based compounds having a large molecular weight is that the fluorene-based compound initiators have relatively low quantum absorbance to long wavelengths.

SUMMARY OF THE INVENTION

A fluorene-based photoinitiator, a preparation method thereof, a photocurable composition having the same, and use thereof in the field of photocuring are discussed to solve the problem of poor photoinitiation properties present in existing photoinitiators.

In order to achieve these objects, a fluorene-based photoinitiator, wherein the fluorene-based photoinitiator has a structure represented by Formula I, or the fluorene-based photoinitiator comprises a structure represented by Formula II is disclosed.

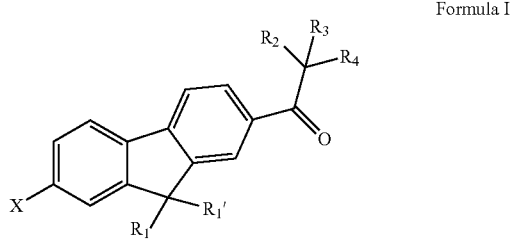

Formula I wherein $R_1$ and $R_1'$ are each independently selected from hydrogen, a halogen, a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group, or a $C_2$-$C_{20}$ alkenyl group; $R_2$ and $R_3$ are each independently selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group, or a $C_6$-$C_{20}$ aryl group; or $R_2$ and $R_3$ are connected to form a $C_3$-$C_8$ cycloalkyl group; X is -A-(X')$_n$, wherein A is selected from a heteroatom which is selected from O, N, or S, X' is selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group or one or more of carbon atoms in X' are substituted with a heteroatom, and n is 1 or 2; and $R_4$ is a hydroxy group or a N-morpholinyl group.

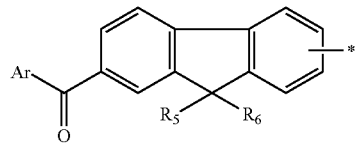

Formula II wherein $R_5$ and $R_6$ are each independently selected from one of a hydrogen atom, a halogen, and a chain group, wherein the chain group is a $C_1$-$C_{20}$ linear alkyl group, a $C_1$-$C_{20}$ branched alkyl group, a $C_1$-$C_{20}$ cycloalkyl group, a $C_4$-$C_{20}$ cycloalkylalkyl group, a $C_4$-$C_{20}$ alkylcycloalkyl group, and a $C_2$-$C_{20}$ alkenyl group, or $R_5$ and $R_6$ form a ring by using one or two of the chain groups, and —$CH_2$— in the chain groups can be substituted with —O—, —C(=O)O—, a halogen, or a phenyl group; Ar is a substituent containing an aromatic ring or a heteroaromatic ring; and $R_7$ connected to a linkage of the group represented by Formula II, wherein $R_7$ is a hydrogen atom, a —C(=O) $R_7'$ group, or a —C(=O)C(=O)O—$R_7'$ group, wherein $R_7'$ represents a $C_1$-$C_{40}$ linear alkyl group, a $C_1$-$C_{40}$ branched alkyl group, a $C_1$-$C_{20}$ cycloalkyl group, a $C_1$-$C_{40}$ alkenyl group, or a substituent containing an aromatic ring or a heteroaromatic ring, which are substituted or unsubstituted, or $R_7$ is a —C(=O)C(=O)O—$R_7'$ group, wherein $R_7'$ group is a group connected by a transesterfication reaction of an alcohol or polyol.

Furthermore, in Formula I, $R_1$ and $R_1'$ are independently selected from hydrogen, a halogen, a $C_1$-$C_{10}$ linear alkyl group, a $C_1$-$C_{10}$ branched alkyl group, a $C_3$-$C_8$ cycloalkyl group, or a $C_1$-$C_{10}$ alkyl group substituted with a $C_3$-$C_8$ cycloalkyl group. In some preferred embodiments, $R_1$ and $R_1'$ are independently selected from hydrogen, a $C_1$-$C_4$ linear alkyl group, a $C_1$-$C_4$ branched alkyl group, or a $C_1$-$C_3$ alkyl group substituted with a $C_3$-$C_6$ cycloalkyl group.

Furthermore, in Formula I, $R_2$ and $R_3$ are each independently selected from a $C_1$-$C_{10}$ linear alkyl group, a $C_1$-$C_{10}$ branched alkyl group, a $C_3$-$C_8$ cycloalkyl group, or a $C_1$-$C_{10}$ alkyl group substituted with a $C_3$-$C_8$ cycloalkyl group; or $R_2$ and $R_3$ are connected to form a $C_3$-$C_{10}$ cycloalkyl group. In some preferred embodiments, $R_2$ and $R_3$ are each independently selected from a $C_1$-$C_4$ linear alkyl group, a $C_1$-$C_4$ branched alkyl group or a $C_4$-$C_8$ cycloalkylalkyl group; or $R_2$ and $R_3$ are connected to form a $C_3$-$C_6$ cycloalkyl group.

In Formula I, X' can be selected from a methyl group, an ethyl group, a cyclohexyl group, or a cyclopentyl group.

Furthermore, the fluorene-based photoinitiator represented by Formula I can be selected from one or more of the following compounds:
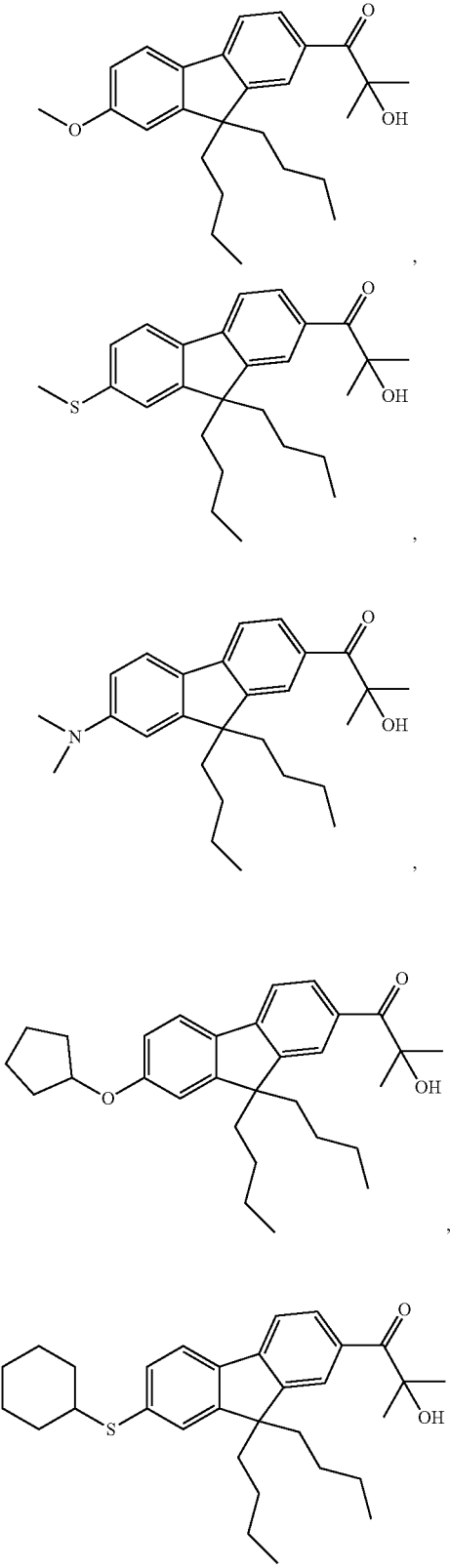
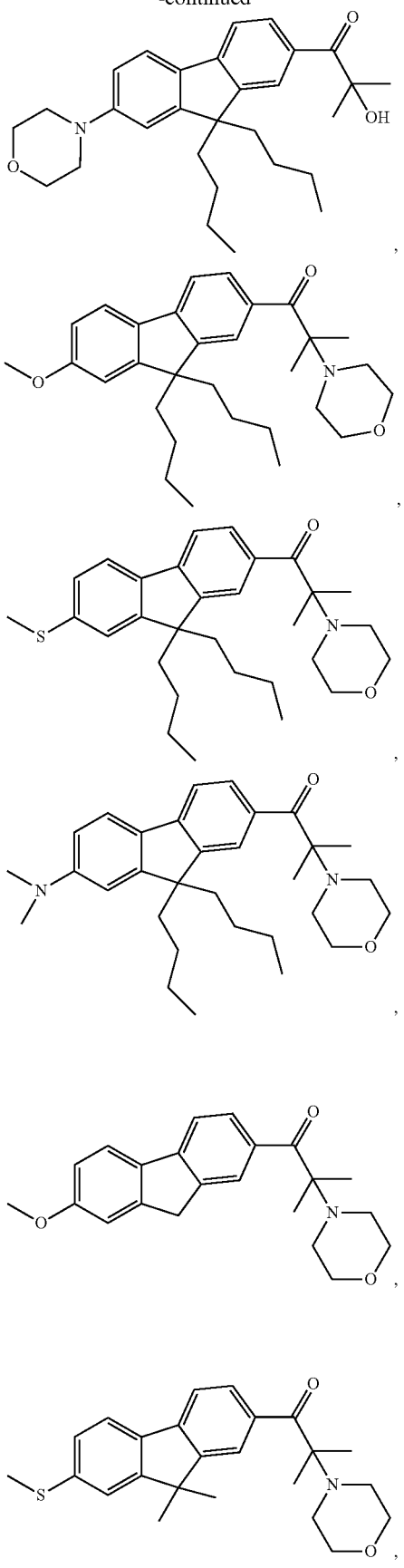

-continued

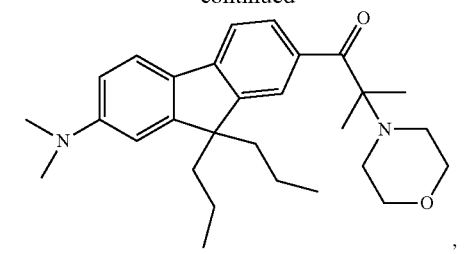,

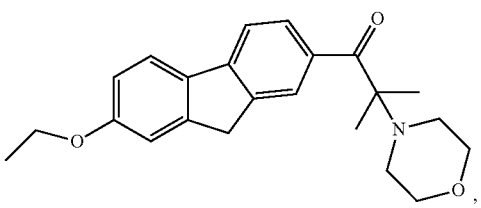,

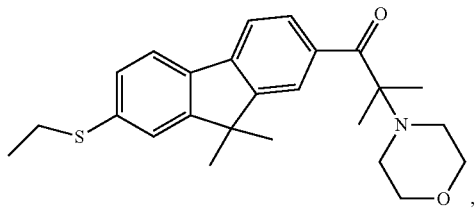,

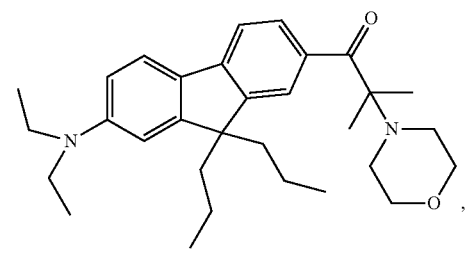,

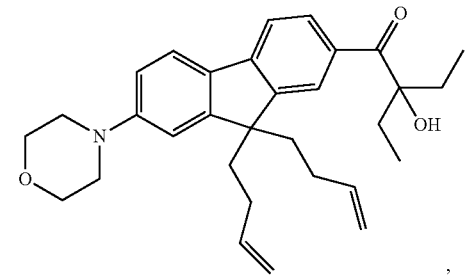,

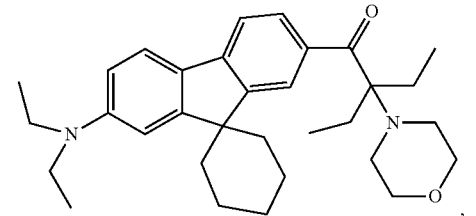,

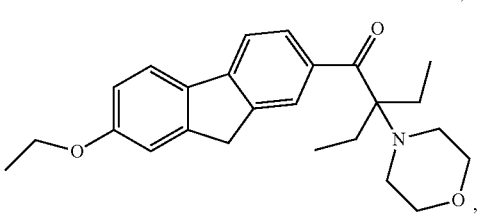,

-continued

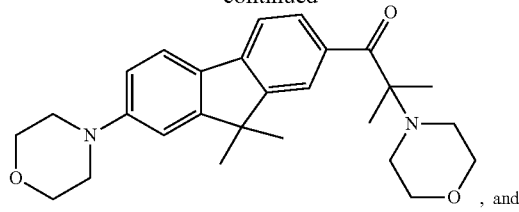, and

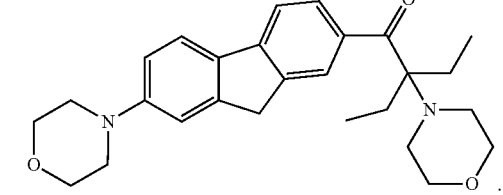.

A preparation method of the fluorene-based photoinitiator having the structure represented by Formula I can comprise: a bromination reaction, wherein Raw Material A, a brominating agent, and a first organic solvent are subjected to a bromination reaction to obtain Intermediate B, wherein Raw Material A has a structure represented by Formula III:

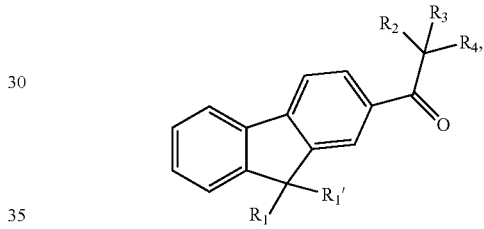

and Intermediate B has a structure of Formula IV:

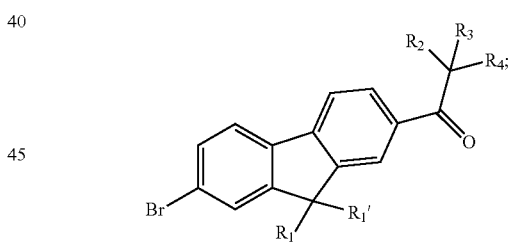

a substitution reaction, wherein Intermediate B, a substituting agent, and a second organic solvent are subjected to a substitution reaction to obtain the fluorene-based photoinitiator, wherein $R_1$ and $R_1'$ are each independently selected from hydrogen, a halogen, a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group, or a $C_2$-$C_{20}$ alkenyl group; $R_2$ and $R_3$ are each independently selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group, or a $C_6$-$C_{20}$ aryl group; or $R_2$ and $R_3$ are connected to form a $C_3$-$C_8$ cycloalkyl group; $R_4$ is a hydroxy group or a N-morpholinyl group.

The brominating agent can be selected from one or more of the group consisting of N-bromosuccinimide, hydrobromic acid, bromine, and dibromohydantoin; preferably, the substituting agent is XONa, and the X is -A-(X')$_n$, wherein A is selected from a heteroatom which is selected from O, N, or S, X' is selected from a C$_1$-C$_{20}$ linear alkyl group, a C$_1$-C$_{20}$ branched alkyl group, a C$_3$-C$_8$ cycloalkyl group, a C$_1$-C$_{10}$ alkyl group substituted with a C$_3$-C$_8$ cycloalkyl group or one or more of carbon atoms in X' are substituted with a heteroatom, and n is 1 or 2.

In the bromination reaction, the first organic solvent can be a polar solvent, preferably propylene carbonate.

In at least some embodiments, the temperature of the bromination reaction is 10-60° C., preferably 25° C.

The second organic solvent can be selected from one or more of the group consisting of dichloromethane, dichloroethane, benzene, and xylene.

A paint composition can comprise a photoinitiator and a photopolymerizable monomer, wherein the photoinitiator is the fluorene-based photoinitiator having the structure represented by Formula I, and the photopolymerizable monomer is an alkenyl-containing compound and/or an epoxy compound.

The photopolymerizable monomer can be an acrylate-based compound. In some preferred embodiments, the photopolymerizable monomer is selected from one or more of the group consisting of an epoxy acrylic resin oligomer, a polyurethane acrylic resin oligomer, and a polyester acrylic resin oligomer.

In at least some embodiments, the paint composition further comprises an auxiliary agent based on parts by weight, wherein the auxiliary agent is selected from one or more of the group consisting of a solvent, a surface adjusting agent, a sensitizing agent, a sensitizer, a curing accelerator, a photo-crosslinking agent, a photosensitizer, a photosensitive resin, a dispersion aid, a filler, a sealing promoter, an antioxidant, an ultraviolet absorbent, a deflocculant, a thermal polymerization inhibitor, a defoaming agent, a leveling agent, a surfactant, and a chain transfer agent.

An ink composition can comprise a photoinitiator, a photopolymerizable monomer, and a pigment, wherein the photoinitiator is the fluorene-based photoinitiator having the structure represented by Formula I, and the photopolymerizable monomer is an alkenyl-containing compound and/or an epoxy compound.

In at least some embodiments, the photopolymerizable monomer is an acrylate-based compound. In some preferred embodiments, the photopolymerizable monomer is selected from one or more of the group consisting of an epoxy acrylic resin oligomer, a polyurethane acrylic resin oligomer, and a polyester acrylic resin oligomer.

In at least some embodiments, the ink composition further comprises an auxiliary agent based on parts by weight, wherein the auxiliary agent is selected from one or more of the group consisting of a solvent, a surface adjusting agent, a sensitizer, a curing accelerator, a photo-crosslinking agent, a sensitizing agent, a photosensitizer, a photosensitive resin, a dispersion aid, a filler, a sealing promoter, an antioxidant, an ultraviolet absorbent, a deflocculant, a thermal polymerization inhibitor, a defoaming agent, a leveling agent, a surfactant, and a chain transfer agent.

In Formula II, the chain group can be a C$_1$-C$_{10}$ linear alkyl group, a C$_1$-C$_{10}$ branched alkyl group, or a C$_4$-C$_{10}$ cycloalkylalkyl group.

In Formula II, Ar can be a phenyl group, a methylphenyl group, an ethylphenyl group, a chlorophenyl group, a bromophenyl group, a methoxyphenyl group, a nitrophenyl group, a cyanophenyl group, a diphenyl sulfide group, a pyridinyl group, a thienyl group, a furanyl group, a 2-methyl-thienyl group, a 3-methylthienyl group, a furanyl group, a 2-methyl-furanyl group, or a 3-methylfuranyl group.

R$_7$ is a —C(═O)C(═O)O—R$_7$' group, and the fluorene-based photoinitiator has a structure represented by Formula V:

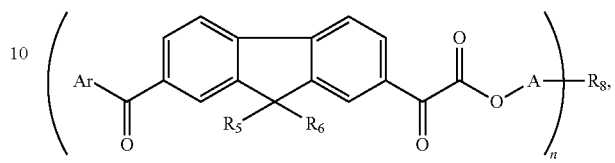

wherein R$_8$ has n external linkages and is a C$_1$-C$_{60}$ linear alkyl group or a C$_1$-C$_{60}$ branched alkyl group, or any carbon or hydrogen in the C$_1$-C$_{60}$ linear alkyl group or the C$_1$-C$_{60}$ branched alkyl group is substituted with oxygen, sulfur, or a phenyl group; A represents a repeating unit having a structure of -(Q-CHR$_9$)$_m$—, wherein R$_9$ is hydrogen, a methyl group, or an ethyl group, Q represents O or a hyphen wherein the hyphen means that —(CHR$_9$)$_m$ is directly connected to O, and m is an integer of 1 to 6; n represents an integer of 1 to 20.

In Formula V, R$_8$ is selected from any one of the following group:

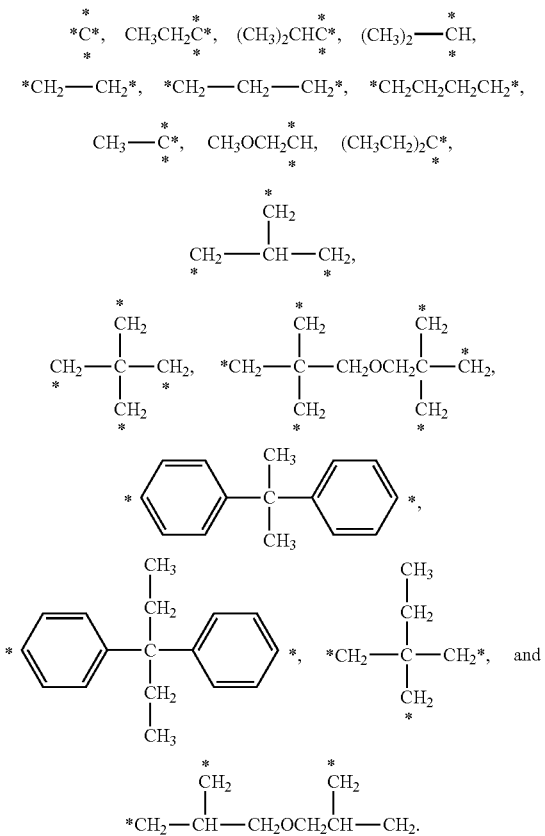

In Formula V, A is selected from -[(Q-CHR$_9$)$_m$]$_y$—, wherein R$_9$ is hydrogen or a methyl group, m is an integer of 1 to 3, and y represents an integer of 1 to 9.

In Formula V, n is an integer of 1 to 8, preferably 1, 2, 3, 4, 5, or 6.

A preparation method of the fluorene-based photoinitiator comprising the structure represented by Formula II can include Step S1, wherein Raw Material A having structural Formula A and Raw Material B having structural Formula B are subjected to a Friedel-Crafts reaction to obtain Intermediate C having structural Formula C; optional Step S2, wherein Intermediate C and Raw Material D having structural Formula D are subjected to a Friedel-Crafts reaction to obtain Intermediate E having structural Formula E; and optional Step S3, wherein Intermediate E and an alcohol or polyol having structural Formula F are subjected to a transesterfication reaction to obtain the fluorene-based photoinitiator, wherein, structural Formula A is

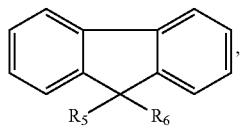

structural Formula B is

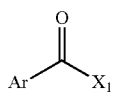

wherein $X_1$ is a halogen,
structural Formula C is

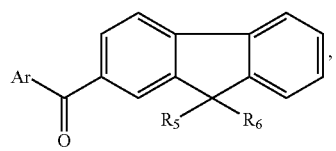

structural Formula D is

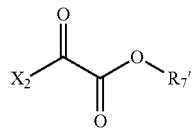

wherein $X_2$ is a halogen,
the structural Formula E is

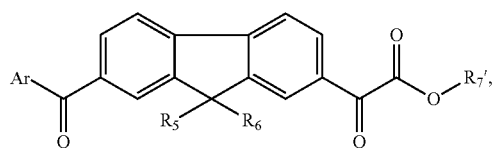

and
the structural Formula F is $R_8(AOH)_n$.

The Friedel-Crafts reactions in Step S1 and Step S2 can be performed in the presence of aluminum trichloride or zinc chloride and a solvent. In at least some preferred embodiments, reaction temperatures of the Friedel-Crafts reactions in Step S1 and Step S2 are each independently −10 to 40° C.

A transesterfication reaction in Step S3 can be performed under the action of a catalyst and a polymerization inhibitor. In some preferred embodiments, the catalyst is a titanic-acid-based compound. In some more preferred embodiments, the catalyst is selected from one or more of the group consisting of 2-ethylhexyl titanate, tetramethyl titanate, tetraisopropyl titanate, tetrabutyl titanate, tetraisobutyl titanate, and tetrakis(2-ethylhexyl) titanate, and the polymerization inhibitor is preferably selected from the group consisting of p-hydroxyanisole, N,N-diethylhydroxylamine, hydroquinone, catechol, p-tert-butylcatechol, methylhydroquinone, p-methoxyphenol, phenothiazine, and triphenylphosphine.

In Step S3, the molar ratio of Intermediate E to the alcohol or polyol having structural Formula F is n:1. In some preferred embodiments, the weight of the catalyst is 3 to 10% of the total weight of materials. In some more preferred embodiments, the weight of the polymerization inhibitor is 3 to 10% of the total weight of the materials, and further preferably the transesterfication reaction has a temperature of 70 to 130° C. and a reaction time of 1 hour to 8 hours.

A photocurable composition can comprise a photoinitiator, wherein the photoinitiator is the fluorene-based photoinitiator comprising the structure represented by Formula II.

Another aspect of this application provides use of the fluorene-based photoinitiator comprising the structure represented by Formula II in the field of photocuring.

Furthermore, uses in paints, inks, adhesives, color photoresists, black matrices, photo-spacers, ribs, dry films, and/or semiconductor photoresists are disclosed.

The introduction of a new group to an existing structure of fluorene not only increases the molecular weight of the photoinitiator, but also improves related properties, such as initiation efficiency and the like, of the photoinitiator.

DETAILED DESCRIPTION OF ILLUSTRATIVE EMBODIMENT(S)

Examples in this application and features in the Examples can be combined with each other without being conflicted.

There are problems of poor properties in existing photoinitiators. In order to solve these technical problems a fluorene-based photoinitiator is disclosed. In some embodiments, the fluorene-based photoinitiator has a structure represented by Formula I:

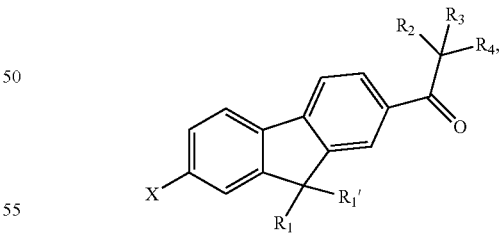

wherein $R_1$ and $R_1'$ are each independently selected from hydrogen, a halogen, a $C_1$-$C_{20}$ linear or branched alkyl group, a $C_3$-$C_8$ cycloalkyl group, a $C_2$-$C_{20}$ alkenyl group, or a $C_1$-$C_{10}$ alkyl group substituted with a $C_3$-$C_8$ cycloalkyl group; $R_2$ and $R_3$ are each independently selected from a $C_1$-$C_{20}$ linear or branched alkyl group, a $C_3$-$C_8$ cycloalkyl group, a $C_1$-$C_{10}$ alkyl group substituted with a $C_3$-$C_8$ cycloalkyl group, or a $C_6$-$C_{20}$ aryl group; or $R_2$ and $R_3$ are connected to form a $C_3$-$C_8$ cycloalkyl group; X is -A-(X')$_n$, wherein A is selected from a heteroatom which is O, N, or S, X' includes but is not limited to a $C_1$-$C_{20}$ linear or branched alkyl group, a $C_3$-$C_{20}$ cycloalkyl group, a $C_3$-$C_{20}$ cycloalkylalkyl group, or a $C_4$-$C_{20}$ cycloalkylalkyl group, and one or more of carbon atoms in X' are substituted with a heteroatom, and n is 1 or 2; and $R_4$ is a hydroxy group or a N-morpholinyl group.

In some embodiments, the fluorene-based photoinitiator comprises a structure represented by Formula II:

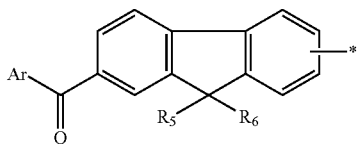

wherein $R_5$ and $R_6$ are each independently selected from any one of a hydrogen atom, a halogen, and a chain group, wherein the chain group is a $C_1$-$C_{20}$ linear alkyl group, a $C_1$-$C_{20}$ branched alkyl group, a $C_1$-$C_{20}$ cycloalkyl group, a $C_4$-$C_{20}$ cycloalkylalkyl group, a $C_4$-$C_{20}$ alkylcycloalkyl group, and a $C_2$-$C_{20}$ alkenyl group, or $R_5$ and $R_6$ form a ring by using one or two of the chain groups, and —$CH_2$— in the chain groups can be substituted with —O—, —C(=O)O—, a halogen, or a phenyl group; and Ar is a substituent containing an aromatic ring or a heteroaromatic ring; and $R_7$ connected to a linkage of the group represented by Formula I, wherein $R_7$ is a hydrogen atom, a —C(=O) $R_7$' group, or a —C(=O)C(=O)O—$R_7$' group, wherein $R_7$' represents a $C_1$-$C_{40}$ linear alkyl group, a $C_1$-$C_{40}$ branched alkyl group, a $C_1$-$C_{20}$ cycloalkyl group, a $C_1$-$C_{40}$ alkenyl group, or a substituent containing an aromatic ring or a heteroaromatic ring, which are substituted or unsubstituted, or $R_7$ is a —C(=O)C(=O)O—$R_7$' group, wherein $R_7$' group is a group connected by a transesterfication reaction of an alcohol or polyol.

Either of the two fluorene-based photoinitiators described above introduces a new group to an existing structure of fluorene, and not only increases the molecular weight of the photoinitiator but also improves related properties, such as initiation efficiency and the like, of the photoinitiator.

In the fluorene-based photoinitiator represented by Formula I, since the group containing a hetero atom (N, S, or O) has an absorption peak at a long wavelength, the introduction of a substituent containing a heteroatom to a side chain of the fluorene-based compound is favorable to the occurrence of red shift of the absorption wavelength of the fluorene-based compound, which can improve the initiation efficiency of the this compound. When the fluorene-based compound containing a hetero atom substituent is used as a photoinitiator, this enables the photoinitiator to have a relatively high quantum absorbance under long-wavelength irradiation. Furthermore, when one or more of carbon atoms in the group X are substituted with a heteroatom, or a hetero atom is contained in another substituent, it is favorable to further improvement in the quantum absorption efficiency of the fluorene-based compound photoinitiator to long wavelengths.

By introducing a micromolecular group to a side chain of the fluorene-based compound in the fluorene-based photoinitiator comprising the group represented by Formula II, the molecular weight of the fluorene-based compound is increased on one hand, and on the other hand, the initiation efficiency of the initiator can be well improved and balanced with the issues such as yellowing resistance, no proneness to migration, low odor property, solubility, and the like. Further, it has been found that when this fluorene-based initiator is used in a current conventional photocurable formulation, it can be well suitable for curing of UV-LED light sources.

Hereinafter, a technical solution related to the fluorene-based photoinitiator represented by Formula I is referred to as a first embodiment, and a technical solution related to the fluorene-based photoinitiator comprising the structure represented by Formula II is referred to as a second embodiment.

In the first embodiment, in Formula I, the fluorene-based photoinitiator having the substituent described above has a relatively high quantum absorption efficiency to long wavelengths. In some preferred embodiments, $R_1$ and $R_1$' are independently selected from hydrogen, a halogen, a $C_1$-$C_{10}$ linear alkyl group, a $C_1$-$C_{10}$ branched alkyl group, or a $C_4$-$C_{10}$ cycloalkylalkyl group; In some preferred embodiments, $R_1$ and $R_1$' independently include but are not limited to hydrogen, a $C_1$-$C_4$ linear alkyl group, a $C_1$-$C_4$ branched alkyl group, or a $C_1$-$C_3$ alkyl group substituted with a $C_3$-$C_6$ cycloalkyl group.

In some preferred embodiments, $R_2$ and $R_3$ are each independently selected from a $C_1$-$C_{10}$ linear alkyl group, a $C_1$-$C_{10}$ branched alkyl group, or a $C_4$-$C_{10}$ cycloalkylalkyl group; or $R_2$ and $R_3$ are connected to form a $C_3$-$C_{10}$ cycloalkyl group. In some preferred embodiments, $R_2$ and $R_3$ are each independently selected from a $C_1$-$C_4$ linear alkyl group, a $C_1$-$C_4$ branched alkyl group, or a $C_4$-$C_8$ cycloalkylalkyl group; or $R_2$ and $R_3$ are connected to form a $C_3$-$C_6$ cycloalkyl group.

In some preferred embodiments, X' includes but is not limited to a methyl group, an ethyl group, a cyclohexyl group, or a cyclopentyl group.

In Formula I, it is favorable to the improvement in the structural stability of the photoinitiator when the groups $R_1$, $R_2$, $R_3$, and X have a small number of carbon atoms. A fluorene-based multifunctional compound having the substituent group described above are more easily synthesized.

In some preferred Examples, the fluorene-based photoinitiator represented by Formula I includes but is not limited to one or more of the following organics:

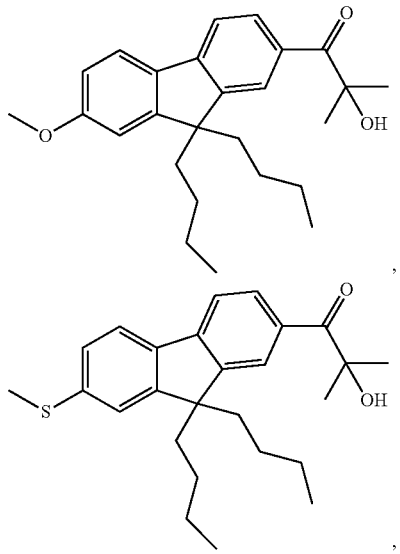

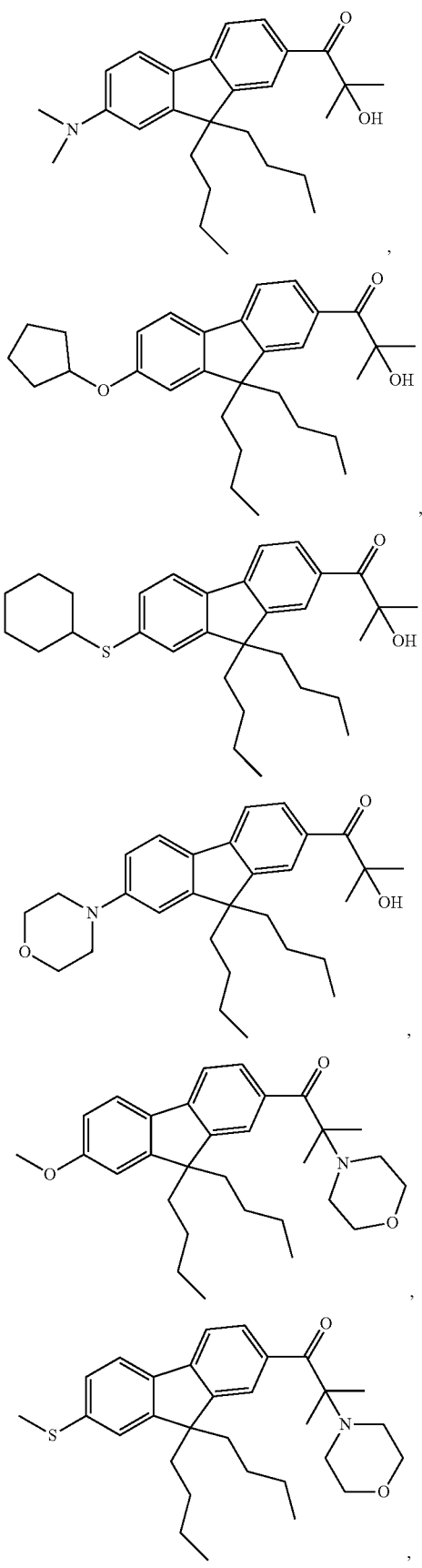
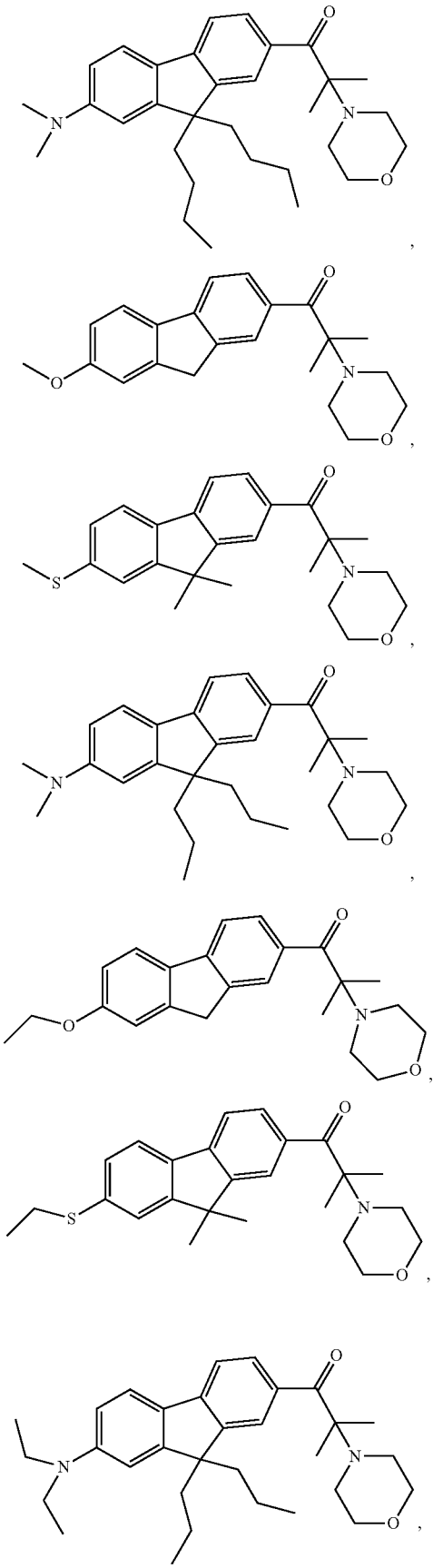

-continued

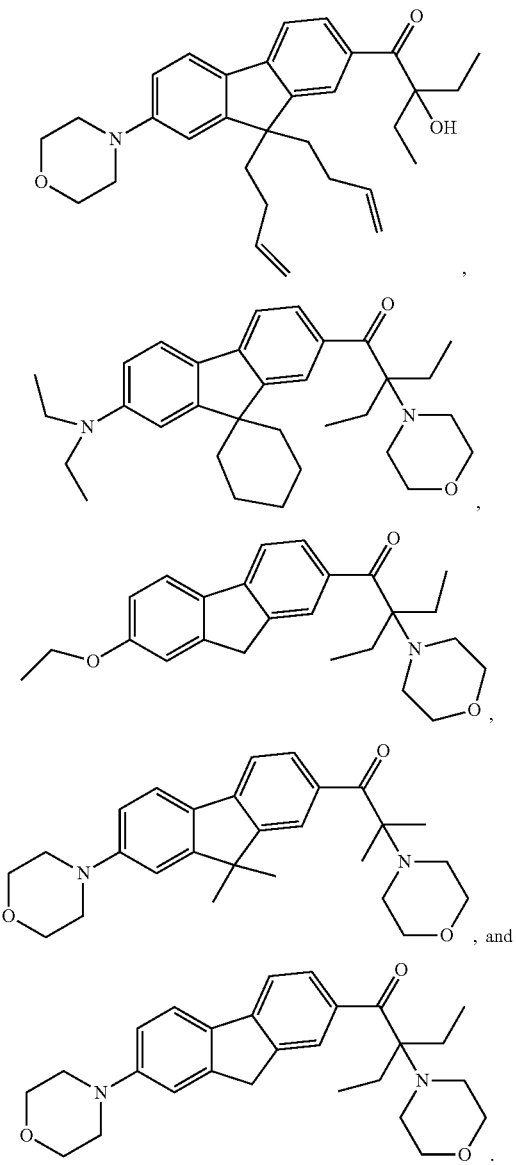

A preparation method of the fluorene-based photoinitiator represented by Formula I, can comprise: a bromination reaction, wherein Raw Material A, a brominating agent, and a first organic solvent are subjected to a bromination reaction to obtain Intermediate B, wherein Raw Material A has a structure represented by Formula III:

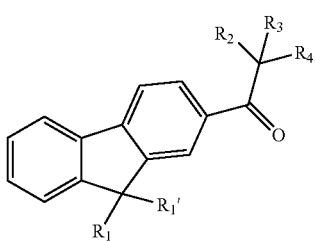

and Intermediate B has a structure of Formula IV:

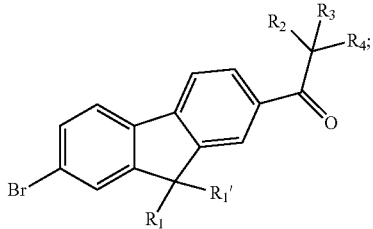

and a substitution reaction, wherein Intermediate B, a substituting agent, and a second organic solvent are subjected to a substitution reaction to obtain the fluorene-based photoinitiator.

The substituent groups $R_1$, $R_2$, $R_3$, $R_4$, and X in the structural formulae represented by Formula III and Formula IV have the same structures as those of the corresponding groups in Formula I. The processes of the chemical reactions in the preparation method described above are as follows:

(1) Bromination Reaction:

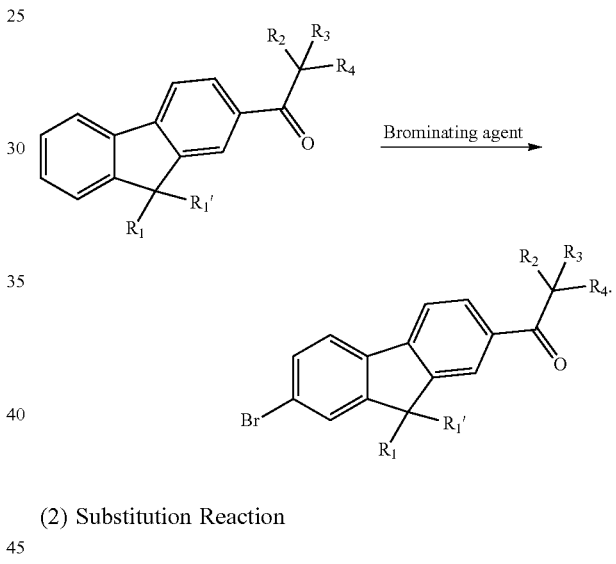

(2) Substitution Reaction

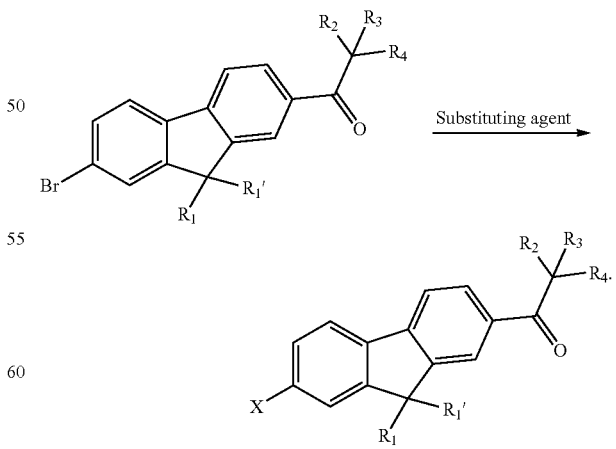

In the preparation method described above, Raw Material A is prepared by a synthesis method disclosed in Patent No. 2015109373280, and other raw materials are compounds which are known and are commercially available, or conveniently prepared by known synthetic methods.

The disclosed fluorene-based photoinitiator can be obtained by the two steps described above, and the reactions involved in the steps (1) and (2) are well-established and commonly used. Therefore, the process of preparation are easily achieved and controlled.

In the preparation method disclosed, the reaction conditions of the bromination reaction and the substitution reaction can be implemented with reference to those of conventional bromination reactions and substitution reactions. With respect to the above substrates, preferably, the brominating agent includes but is not limited to one or more of the group consisting of N-bromosuccinimide, hydrobromic acid, bromine, and dibromohydantoin; preferably, the substituting agent is XONa, and the X is -A-(X')$_n$, wherein A is selected from a heteroatom which is selected from O, N, or S, X' is selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group or one or more of carbon atoms in X' are substituted with the heteroatom described above, and n is 1 or 2.

In some preferred embodiments, the reaction system is a polar solvent system, a Lewis acid can be selectively added as a catalyst in the reaction, and the first organic solvent is preferably propylene carbonate; and preferably, the temperature of the bromination reaction is 10-60° C., preferably 25° C.

Commonly used organic solvents, which is are involved in the reaction, can be often used as the second organic solvent used in the substitution reaction. In some preferred embodiments, the second organic solvent includes but is not limited to one or more of the group consisting of dichloromethane, dichloroethane, benzene, and xylene.

A paint composition can comprise a photoinitiator and a photopolymerizable monomer, wherein the photoinitiator is the fluorene-based photoinitiator represented by Formula I, and the photopolymerizable monomer is an alkenyl-containing compound and/or an epoxy compound.

In at least some embodiment, the curing mechanism of the paint composition described above is that the photoinitiator is activated under light irradiation; and the photopolymerizable monomer is then polymerized by the activated initiator so as to form a film by curing.

Since the fluorene-based photoinitiator represented by Formula I has a relatively high quantum absorption efficiency to long wavelengths, the paint composition containing the disclosed photoinitiator has the advantages of low curing energy, high curing efficiency, and the like in the process of photocuring.

During the practical use of the paint composition described above, the disclosed photoinitiator provided can be compounded with a commonly used initiator.

In some preferred examples, the photopolymerizable monomer is an acrylate-based compound; preferably, the photopolymerizable monomer includes but is not limited to one or more of the group consisting of an epoxy acrylic resin oligomer, a polyurethane acrylic resin oligomer, and a polyester acrylic resin oligomer.

In some more preferred examples, the photopolymerizable monomer described above includes but is not limited to one or more of the group consisting of methyl (meth)acrylate, ethyl (meth)acrylate, butyl (meth)acrylate, 2-ethylhexyl (meth)acrylate, cyclohexyl (meth)acrylate, 2-hydroxyethyl (meth)acrylate, 2-hydroxypropyl (meth)acrylate, 2-hydroxybutyl (meth)acrylate, 2-phenoxy-2-hydroxypropyl (meth)acrylate, 2-(meth)acryloxy-2-hydroxypropyl phthalate, glycerol mono(meth)acrylate, tetrahydrofurfuryl (meth)acrylate, dimethylamino(meth)acrylate, glycidyl (meth)acrylate, 2,2,2-trifluoroethyl (meth)acrylate, 2,2,3,3-tetrafluoropropyl (meth)acrylate, (meth)acrylic acid hemiesters of phthalic acid derivatives, 1,3-butanediol di(meth)acrylate, 1,4-butanediol di(meth)acrylate, 1,6-hexanediol di(meth)acrylate, 1,9-nonanediol di(meth)acrylate, 1,10-decanediol di(meth)acrylate, 1,12-dodecanediol di(meth)acrylate, ethoxylated hexanediol di(meth)acrylate, tricyclodecanedimethanol di(meth)acrylate, 2-hydroxy-3-(meth)acryloxypropyl (meth)acrylate, dipentaerythritol di(meth)acrylate, diethylene glycol di(meth)acrylate, triethylene glycol di(meth)acrylate, dipropylene glycol di(meth)acrylate, tripropylene glycol di(meth)acrylate, ethoxylated neopentyl glycol di(meth)acrylate, polyethylene glycol di(meth)acrylate, poly(ethylene-propylene)diol di(meth)acrylate, poly(1,4-butanediol) di(meth)acrylate, ethoxylated bisphenol A di(meth)acrylate, propoxylated bisphenol A di(meth)acrylate, propoxylated ethoxylated bisphenol A di(meth)acrylate, ethylene glycol di(meth)acrylate, diethylene glycol di(meth)acrylate, tetraethylene glycol di(meth)acrylate, propylene glycol di(meth)acrylate, polypropylene glycol di(meth)acrylate, butanediol di(meth)acrylate, neopentyl glycol di(meth)acrylate, 1,6-hexanediol di(meth)acrylate, trimethylolpropane tri(meth)acrylate, glycerol di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri(meth)acrylate, pentaerythritol tetra(meth)acrylate, dipentaerythritol penta(meth)acrylate, dipentaerythritol hexa(meth)acrylate, 2,2-bis(4-(meth)acryloxydiethoxyphenyl)propane, 2,2-bis(4-(meth)acryloxypolyethoxyphenyl)propane, 2-hydroxy-3-(meth)acryloxypropyl (meth)acrylate, ethylene glycol diglycidyl ether di(meth)acrylate, diethylene glycol diglycidyl ether di(meth)acrylate, diglycidyl phthalate di(meth)acrylate, glycerol triacrylate, glycerol polyglycidyl ether poly(meth)acrylate, urethane (meth)acrylate (i.e., tolylene diisocyanate), reaction products of trimethyl-1,6-hexamethylene diisocyanate, 1,6-hexamethylene diisocyanate, and the like with 2-hydroxyethyl (meth)acrylate, methylenebis(meth)acrylamide, (meth)acrylamide methylene ether, condensates of polyols and N-hydroxymethyl (meth)acrylamide, 1,3,5-triacrylhexahydro-1,3,5-triazine, 2,4,6-trioxohexahydro-1,3,5-triazine-1,3,5-triethanol triacrylate, and 2,4,6-trioxohexahydro-1,3,5-triazine-1,3,5-triethanol diacrylate.

In some preferred examples, the paint composition further comprises an auxiliary agent based on parts by weight, wherein the auxiliary agent includes but is not limited to one or more of the group consisting of a solvent, a surface adjusting agent, a sensitizing agent, a sensitizer, a curing accelerator, a photo-crosslinking agent, a photosensitizer, a photosensitive resin, a dispersion aid, a filler, a sealing promoter, an antioxidant, an ultraviolet absorbent, a deflocculant, a thermal polymerization inhibitor, a defoaming agent, a leveling agent, a surfactant, and a chain transfer agent. The addition of the auxiliary agent is favorable to the improvement in overall properties of the paint composition.

Furthermore, in consideration of factors such as cost and the like, the disclosed photoinitiator can also be used in combination with other photoinitiators.

An ink composition can comprise a photoinitiator, a photopolymerizable monomer, and a pigment. In at least some embodiments, the photoinitiator is the fluorene-based photoinitiator represented by Formula I, and the photopolymerizable monomer is an alkenyl-containing compound and/or an epoxy compound.

The curing mechanism of the ink composition described above is that the photoinitiator is activated in the light; and the photopolymerizable monomer is then polymerized by the activated initiator to form a film by curing.

Since the fluorene-based photoinitiator represented by Formula I has a relatively high quantum absorption efficiency to long wavelengths, the ink composition containing the photoinitiator has the advantages of low curing energy, high curing efficiency, and the like in the process of photocuring.

During the practical use of the ink composition described above, the photoinitiator provided in this application can be compounded with a commonly used initiator.

In some preferred example, the photopolymerizable monomer is an acrylate-based compound; preferably, the photopolymerizable monomer includes but is not limited to one or more of the group consisting of an epoxy acrylic resin oligomer, a polyurethane acrylic resin oligomer, and a polyester acrylic resin oligomer.

In some more preferred embodiments, the photopolymerizable monomer includes but is not limited to the photopolymerizable monomer described above which includes but is not limited to one or more of the group consisting of methyl (meth)acrylate, ethyl (meth)acrylate, butyl (meth)acrylate, 2-ethylhexyl (meth)acrylate, cyclohexyl (meth)acrylate, 2-hydroxyethyl (meth)acrylate, 2-hydroxypropyl (meth)acrylate, 2-hydroxybutyl (meth)acrylate, 2-phenoxy-2-hydroxypropyl (meth)acrylate, 2-(meth)acryloxy-2-hydroxypropyl phthalate, glycerol mono(meth)acrylate, tetrahydrofurfuryl (meth)acrylate, dimethylamino(meth)acrylate, glycidyl (meth)acrylate, 2,2,2-trifluoroethyl (meth)acrylate, 2,2,3,3-tetrafluoropropyl (meth)acrylate, (meth)acrylic acid hemiesters of phthalic acid derivatives, 1,3-butanediol di(meth)acrylate, 1,4-butanediol di(meth)acrylate, 1,6-hexanediol di(meth)acrylate, 1,9-nonanediol di(meth)acrylate, 1,10-decanediol di(meth)acrylate, 1,12-dodecanediol di(meth)acrylate, ethoxylated hexanediol di(meth)acrylate, tricyclodecanedimethanol di(meth)acrylate, 2-hydroxy-3-(meth)acryloxypropyl (meth)acrylate, dipentaerythritol di(meth)acrylate, diethylene glycol di(meth)acrylate, triethylene glycol di(meth)acrylate, dipropylene glycol di(meth)acrylate, tripropylene glycol di(meth)acrylate, ethoxylated neopentyl glycol di(meth)acrylate, polyethylene glycol di(meth)acrylate, poly(ethylene-propylene) diol di(meth) acrylate, poly(1,4-butanediol) di(meth) acrylate, ethoxylated bisphenol A di(meth)acrylate, propoxylated bisphenol A di(meth)acrylate, propoxylated ethoxylated bisphenol A di(meth)acrylate, ethylene glycol di(meth)acrylate, diethylene glycol di(meth)acrylate, tetraethylene glycol di(meth)acrylate, propylene glycol di(meth) acrylate, polypropylene glycol di(meth)acrylate, butanediol di(meth)acrylate, neopentyl glycol di(meth)acrylate, 1,6-hexanediol di(meth)acrylate, trimethylolpropane tri(meth)acrylate, glycerol di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri(meth)acrylate, pentaerythritol tetra(meth)acrylate, dipentaerythritol penta(meth)acrylate, dipentaerythritol hexa(meth)acrylate, 2,2-bis(4-(meth)acryloxydiethoxyphenyl)propane, 2,2-bis(4-(meth)acryloxypolyethoxyphenyl)propane, 2-hydroxy-3-(meth)acryloxypropyl (meth)acrylate, ethylene glycol diglycidyl ether di(meth)acrylate, diethylene glycol diglycidyl ether di(meth)acrylate, diglycidyl phthalate di(meth) acrylate, glycerol triacrylate, glycerol polyglycidyl ether poly(meth)acrylate, urethane (meth)acrylate (i.e., tolylene diisocyanate), reaction products of trimethyl-1,6-hexamethylene diisocyanate, 1,6-hexamethylene diisocyanate, and the like with 2-hydroxyethyl (meth)acrylate, methylenebis (meth)acrylamide, (meth)acrylamide methylene ether, condensates of polyols and N-hydroxymethyl (meth)acrylamide, 1,3,5-triacrylhexahydro-1,3,5-triazine, 2,4,6-trioxohexahydro-1,3,5-triazine-1,3,5-triethanol triacrylate, and 2,4,6-trioxohexahydro-1,3,5-triazine-1,3,5-triethanol diacrylate.

In some preferred examples, the ink composition further comprises an auxiliary agent based on parts by weight, wherein the auxiliary agent includes but is not limited to one or more of the group consisting of a solvent, a surface adjusting agent, a sensitizing agent, a sensitizer, a curing accelerator, a photo-crosslinking agent, a photosensitizer, a photosensitive resin, a dispersion aid, a filler, a sealing promoter, an antioxidant, an ultraviolet absorbent, a deflocculant, a thermal polymerization inhibitor, a defoaming agent, a leveling agent, a surfactant, and a chain transfer agent. The addition of the auxiliary agent is favorable to the improvement in overall properties of the ink composition.

In the second embodiment, in Formula II, the chain group is a $C_1$-$C_{10}$ linear alkyl group, a $C_1$-$C_{10}$ branched alkyl group, or a $C_4$-$C_{10}$ cycloalkylalkyl group.

Preferably, in Formula II, Ar is a phenyl group, a methylphenyl group, an ethylphenyl group, a chlorophenyl group, a bromophenyl group, a methoxyphenyl group, a nitrophenyl group, a cyanophenyl group, a diphenyl sulfide group, a pyridinyl group, a thienyl group, a furanyl group, a 2-methyl-thienyl group, a 3-methylthienyl group, a furanyl group, a 2-methyl-furanyl group, or a 3-methylfuranyl group.

Preferably, $R_7$ is a —C(=O)C(=O)O—$R_7$' group, and the fluorene-based photoinitiator has a structure represented by Formula V:

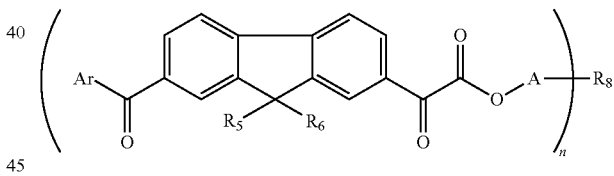

wherein $R_8$ has n external linkages and is a $C_1$-$C_{60}$ linear alkyl group, a $C_1$-$C_{60}$ branched alkyl group, or any carbon or hydrogen in the $C_1$-$C_{60}$ linear or branched alkyl group is substituted with oxygen, sulfur, or a phenyl group;

A represents a repeating unit having a structure of -(Q-CHR$_9$)$_m$—, wherein $R_9$ is hydrogen, a methyl group, or an ethyl group, Q represents O or a hyphen wherein the hyphen means that —(CHR$_9$)$_m$ is directly connected to O, and m is an integer of 1 to 6; and n represents an integer of 1 to 20.

The fluorene-based photoinitiator having the structural Formula V is not only allowed to have a reduced mobility due to its larger molecular weight, but also has a characteristic of more excellent solubility.

Additionally, either of the photoinitiator having the group represented by Formula II described above and the photoinitiator having the structure represented by Formula V has an absorption band between 330 nm and 400 nm, almost no odor, very good solubilities in both of (meth)acrylic resins and vinyl ether-based compounds, no proneness to migration after application, and yellowing resistance.

In Formula V, $R_8$ has a more stable structure when it is selected from one of the following groups:

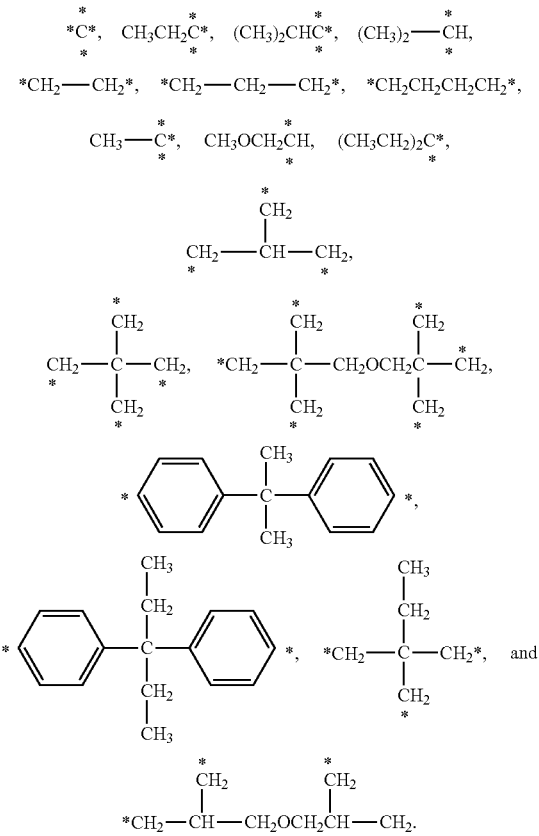

In some preferred embodiments, in Formula V, A is selected from -[(Q-CHR$_9$)$_m$]$_y$—, wherein $R_9$ is hydrogen or a methyl group, m is an integer of 1 to 3, and y represents an integer of 1 to 9.

In some preferred embodiments, in Formula V, n is an integer of 1 to 8, preferably 1, 2, 3, 4, 5, or 6.

In some preferred embodiments, the preparation method of the photoinitiator having the group represented by Formula II comprises: Step S1, wherein Raw Material A having structural formula A and Raw Material B having structural Formula B are subjected to a Friedel-Crafts reaction to obtain Intermediate C having structural Formula C; optional Step S2, wherein Intermediate C and Raw Material D having structural Formula D are subjected to a Friedel-Crafts reaction to obtain Intermediate E having structural Formula E; and optional Step S3, wherein Intermediate E and an alcohol or polyol having structural Formula F are subjected to a transesterfication reaction to obtain the fluorene-based photoinitiator,
wherein the structural Formula A is

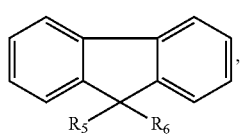

the structural Formula B is

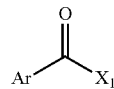

wherein the $X_1$ is a halogen,
the structural Formula C is

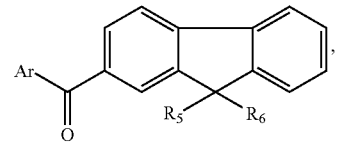

the structural Formula D is

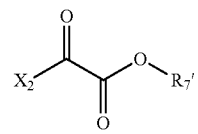

wherein the $X_2$ is a halogen,
the structural Formula E is

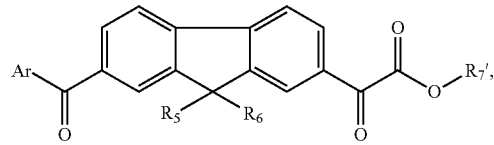

and the structural Formula F is $R_8(AOH)_n$.

All of R5, R6, Ar, R7, R7', and R8 in the structural formulae described above are the same as the corresponding groups represented by the structural Formula II and the structural Formula V.

The processes of the chemical reactions in the preparation method described above are as follows:

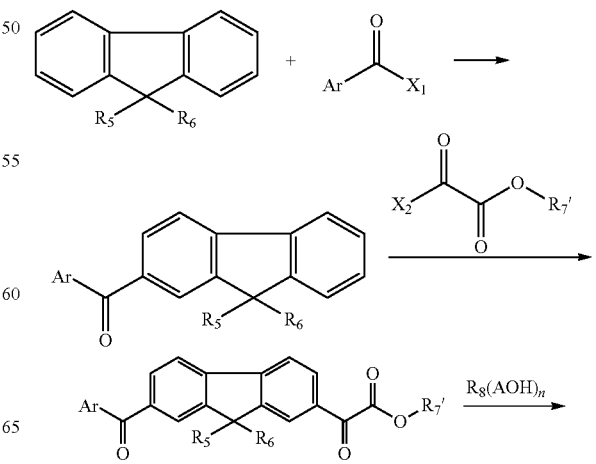

-continued

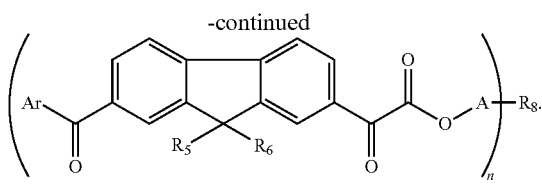

Various fluorene-based photoinitiators can be obtained by one step, two steps, or three steps described above, and the reactions used in each step are well-established. Therefore, the process of preparation can be easily achieved and controlled. Here, when n in $R_8(AOH)_n$ is an integer greater than 1, a plurality of intermediates E and $R_8(AOH)_n$ are subjected to transesterfication reactions simultaneously to obtain the product described above.

In at least some embodiments, the Friedel-Crafts reactions in Step S1 and Step S2 described above are performed in the presence of aluminum trichloride or zinc chloride and a solvent, and preferably, reaction temperatures of the Friedel-Crafts reactions in Step S1 and Step S2 are each independently −10 to 40° C. In the Friedel-Crafts reactions in the two steps described above, the conditions can be the same or can be different, and the solvents can be the same or can be different. Here, a commonly used organic solvent, which does not interfere with the reaction, can be used as the solvent, for example dichloromethane, dichloroethane, toluene, benzene, and xylene. When the two steps employ the same solvent, the Friedel-Crafts reaction of Step S2 can continue to be performed without performing purification after the completion of Step S1.

The transesterfication reaction of Step S3 described above can be directly performed in the system where Step S2 is finished or can be performed by placing in a solvent again after purification. In the application, the solvent of Step S3 is not particularly limited, as long as it can dissolve reactive agents and there is no adverse influence on the reaction, for example toluene, benzene, and xylene.

In order to accelerate the reaction and in order to obtain products of interest and reduce generation of byproducts, the transesterfication reaction in Step S3 described above is preferably performed under the action of a catalyst and a polymerization inhibitor, wherein the catalyst is preferably a titanic-acid-based compound and the catalyst is more preferably selected from one or more of the group consisting of 2-ethylhexyl titanate, tetramethyl titanate, tetraisopropyl titanate, tetrabutyl titanate, tetraisobutyl titanate, and tetrakis (2-ethylhexyl) titanate, and the polymerization inhibitor is preferably selected from one of the group consisting of p-hydroxyanisole, N,N-diethylhydroxylamine, hydroquinone, catechol, p-tert-butylcatechol, methylhydroquinone, p-methoxyphenol, phenothiazine, and triphenylphosphine.

Additionally, in order to save raw materials on the basis that the yield of products of interest has been ensured, preferably in Step S3 described above, the molar ratio of Intermediate E to the alcohol or polyol having structural Formula F is n:1, preferably the weight of the catalyst is 3 to 10% of the total weight of materials, more preferably the weight of the polymerization inhibitor is 3 to 10% of the total weight of the materials, and further preferably the transesterfication reaction has a temperature of 70 to 130° C. and a reaction time of 1 hour to 8 hours.

A photocurable composition can comprise a photoinitiator, wherein this photoinitiator is the fluorene-based photoinitiator comprising the structure represented by Formula II.

With respect to the fluorene-based photoinitiator comprising the structure represented by Formula II, the initiation efficiency of the initiator can be well improved and balanced with issues such as yellowing resistance, no proneness to migration, low odor property, solubility, and the like, relative to benzophenone- or benzoylformate-based initiators. Therefore, when it is used in a composition, it enables the structure formed by the composition to have more stable properties and enables this photocurable composition to be cured under irradiation of a UV-LED light source, so that energy is saved and it more complies with requirements for environmental protection.

Uses of the fluorene-based photoinitiator comprising the structure represented by Formula II in the field of photocuring are disclosed.

The fluorene-based photoinitiator comprising the structure represented by Formula II enables the photocurable composition having the same to be cured under irradiation of a UV-LED light source, so that the use containing the same saves energy and it more complies with requirements for environmental protection. In some preferred embodiments, the use described above comprises use in paints, inks, adhesives, color photoresists, black matrices, photo-spacers, ribs, dry films, and/or semiconductor photoresists.

Specific examples are listed below for illustrative purposes. These examples should not be construed as limiting.

(I) Preparation Scheme and Property Evaluation Related to Fluorene-Based Photoinitiator Represented by Formula I.

1. Preparation of Photoinitiator.

Preparation Example 1

(1) Substitution Reaction: Preparation of Intermediate 1a.

36.5 g of the raw material 1a, 18 g of N-bromosuccinimide, and 100 mL of propylene carbonate were added to a 500 mL four-neck flask, and stirred at room temperature. Liquid phase tracking was performed on the reaction until the raw materials did not change. The materials were then slowly poured into 1000 g of deionized water with stirring to precipitate a large amount of solid. Suction filtration, water washing, and absolute ethanol were performed to obtain 37.2 g of the intermediate 1a. The synthetic scheme was as follows:

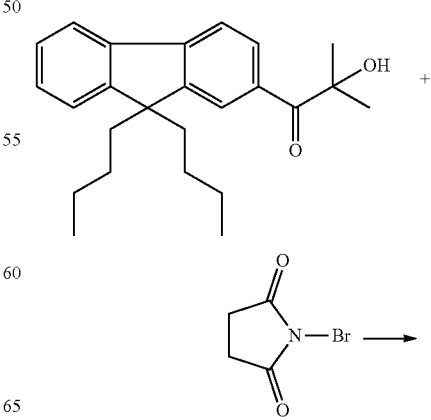

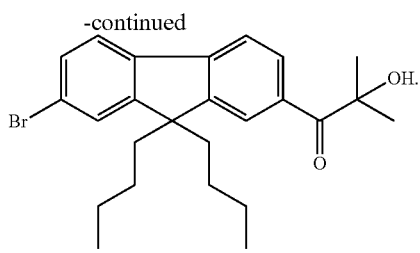

The structure characterization data of this intermediate 1a was as shown below: $^1$H-NMR (CDCl$_3$, 500 MHz): 0.9146-1.0002 (6H, t), 1.2878-1.3328 (8H, m), 1.4844 (6H, s), 1.8754-2.1045 (5H, m), 7.5801-8.0837 (6H, m); MS (m/z): 444 (M+1)$^+$.

(2) Substitution Reaction: Preparation of Compound 1.

22.2 g of the intermediate 1a, 50 mL of methanol, and 14.0 g of sodium methoxide were added to a 500 mL four-neck flask, and stirred at room temperature. Liquid phase tracking was performed on the reaction until the amount of the raw materials did not change. The reaction liquid was then poured into 500 mL of deionized water to precipitate a product. Water washing and recrystallization with methanol were performed to obtain 15.5 g of a white solid, which was the compound 1. The synthetic scheme was as follows:

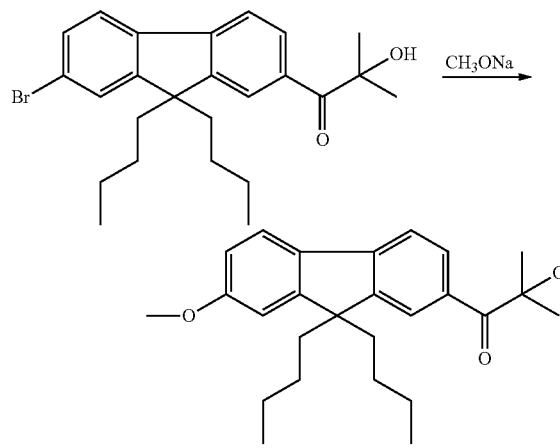

The structure characterization data of the compound 1 was as shown below: $^1$H-NMR (CDCl$_3$, 500 MHz): 1.6642 (6H, s), 2.0629 (6H, s), 7.3080-7.8346 (7H, m); MS (m/z): 3: 95 (M+1)$^+$.

Preparation Example 2

Substitution reaction: preparation of intermediate 2a.

35.0 g of the raw material 2a, 18 g of N-bromosuccinimide, and 100 mL of propylene carbonate were added to a 500 mL four-neck flask, and stirred at room temperature. Liquid phase tracking was performed on the reaction until the raw materials did not change. The materials were then slowly poured into 1000 g of deionized water with stirring to precipitate a large amount of solid. Suction filtration, water washing, and absolute ethanol were performed to obtain 36.8 g of the intermediate 2a. The synthetic scheme was as follows:

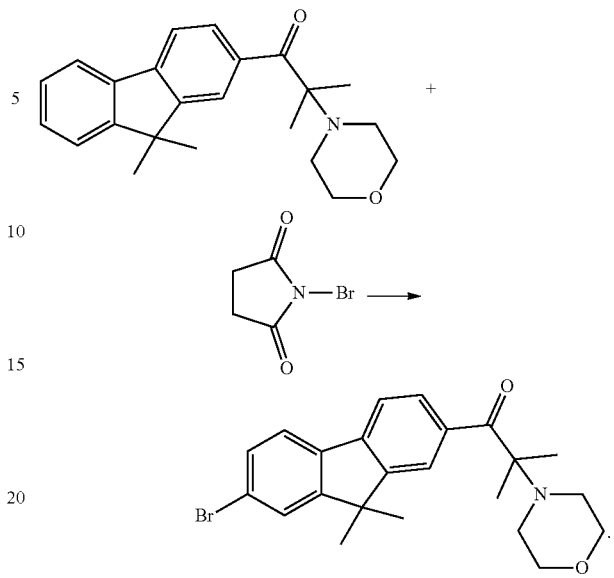

The structure characterization data of this intermediate 2a was as shown below: $^1$H-NMR (CDCl$_3$, 500 MHz): 1.3629 (6H, s), 1.6578 (6H, s), 2.3899-2.3835 (4H, t), 3.6703-3.6801 (4H, t), 7.5481-7.8997 (6H, m); MS (m/z): 429 (M+1)$^+$.

(2) Substitution Reaction: Preparation of Compound 2.

21.4 g of the intermediate 2a, 50 mL of xylene, and 14.0 g of sodium methoxide were added to a 500 mL four-neck flask, followed by heating under reflux at 100° C. A reaction was performed at a reduced pressure (1 Mpa). Liquid phase tracking was performed on the reaction until the amount of the raw materials did not change. The reaction liquid was then poured into 500 mL of deionized water to precipitate a product. Water washing and recrystallization with methanol were performed to obtain 16.7 g of a white solid, which was the compound 2. The synthetic scheme was as follows:

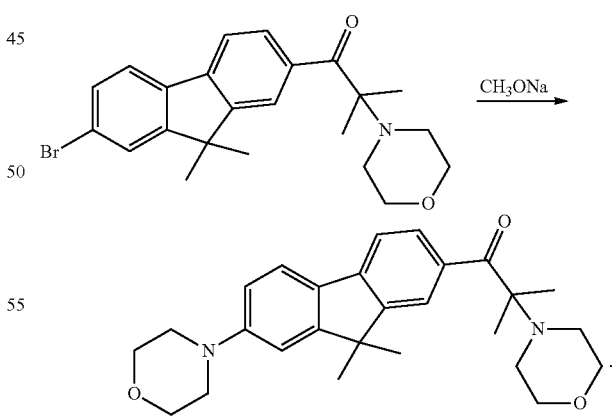

The structure characterization data of the compound 2 was as shown below:

$^1$H-NMR (CDCl$_3$, 500 MHz): 1.3702 (6H, s), 1.6695 (6H, s), 2.3693-2.3742 (4H, t), 2.8994-2.9347 (4H, m), 3.6548-3.6775 (8H, m), 6.8303-7.9403 (6H, m); MS (m/z): 435 (M+1)$^+$.

Preparation Examples 3 to 20

Compounds 3 to 20 having different structures were prepared by selecting different raw materials with reference to the synthesis method of Example 1 or 2. The structures of the compounds 3 to 20 are shown in Table 1.

TABLE 1

| | Structure | MS(m/z) |
|---|---|---|
| Compound 3 | 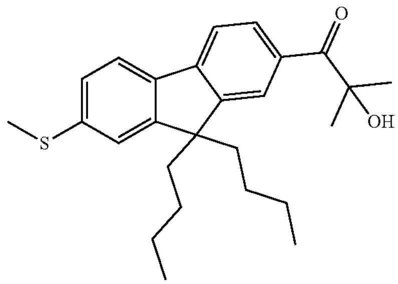 [SMILES: CCCCC1(CCCC)c2cc(SC)ccc2-c2ccc(C(=O)C(C)(C)O)cc21] | 411 |
| Compound 4 | 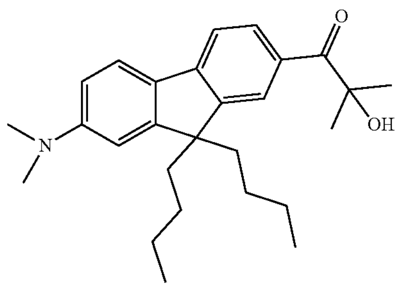 [SMILES: CCCCC1(CCCC)c2cc(C(=O)C(C)(C)O)ccc2-c2ccc(N(C)C)cc21] | 408 |
| Compound 5 | 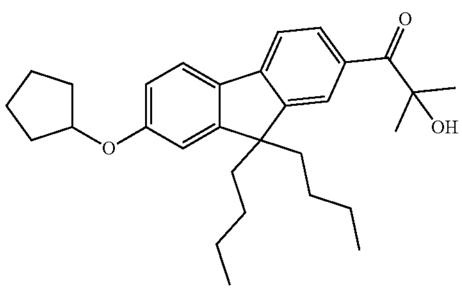 [SMILES: CCCCC1(CCCC)c2cc(OC3CCCC3)ccc2-c2ccc(C(=O)C(C)(C)O)cc21] | 449 |
| Compound 6 | 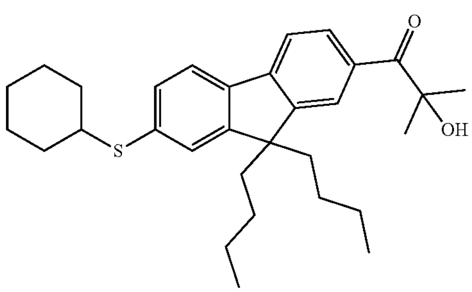 [SMILES: CCCCC1(CCCC)c2cc(SC3CCCCC3)ccc2-c2ccc(C(=O)C(C)(C)O)cc21] | 479 |
| Compound 7 | 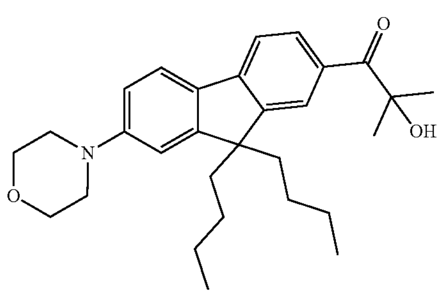 [SMILES: CCCCC1(CCCC)c2cc(C(=O)C(C)(C)O)ccc2-c2ccc(N3CCOCC3)cc21] | 450 |

TABLE 1-continued

| | Structure | MS(m/z) |
|---|---|---|
| Compound 8 | 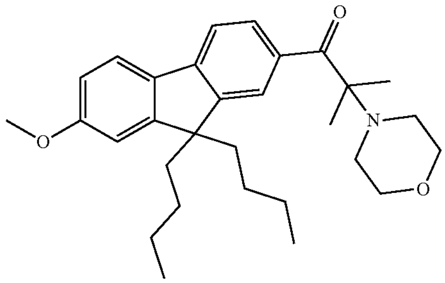 [SMILES: CCCCC1(CCCC)c2cc(OC)ccc2-c2ccc(C(=O)C(C)(C)N3CCOCC3)cc21] | 464 |
| Compound 9 | 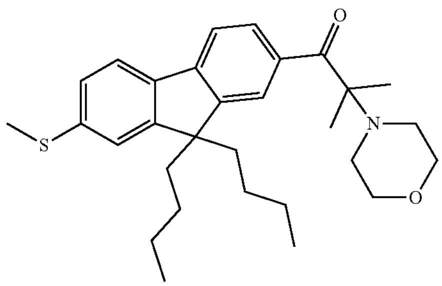 [SMILES: CCCCC1(CCCC)c2cc(SC)ccc2-c2ccc(C(=O)C(C)(C)N3CCOCC3)cc21] | 480 |
| Compound 10 | 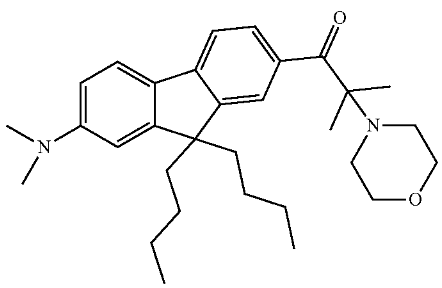 [SMILES: CCCCC1(CCCC)c2cc(C(=O)C(C)(C)N3CCOCC3)ccc2-c2ccc(N(C)C)cc21] | 477 |
| Compound 11 | 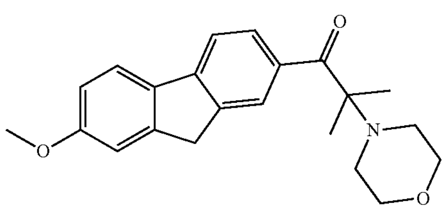 [SMILES: COc1ccc2c(c1)Cc1cc(C(=O)C(C)(C)N3CCOCC3)ccc1-2] | 352 |
| Compound 12 | 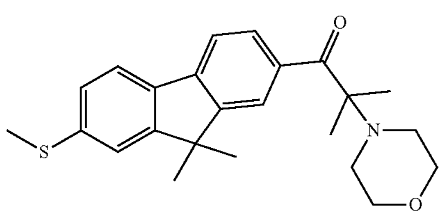 [SMILES: CSc1ccc2c(c1)C(C)(C)c1cc(C(=O)C(C)(C)N3CCOCC3)ccc1-2] | 396 |
| Compound 13 | 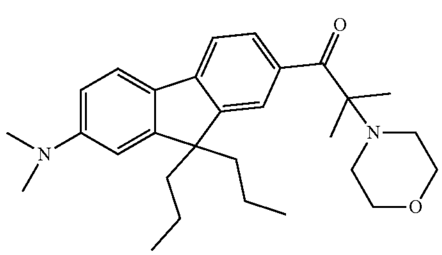 [SMILES: CCCC1(CCC)c2cc(C(=O)C(C)(C)N3CCOCC3)ccc2-c2ccc(N(C)C)cc21] | 449 |

TABLE 1-continued

| | Structure | MS(m/z) |
|---|---|---|
| Compound 14 | 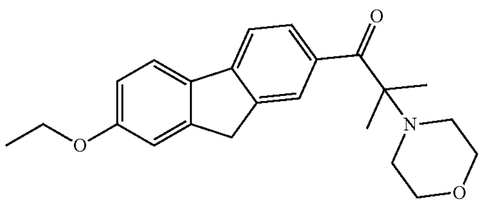 [SMILES: CCOc1ccc2c(c1)Cc1cc(C(=O)C(C)(C)N3CCOCC3)ccc1-2] | 366 |
| Compound 15 | 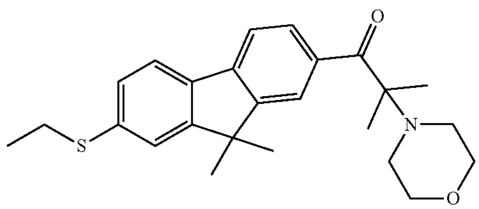 [SMILES: CCSc1ccc2c(c1)C(C)(C)c1cc(C(=O)C(C)(C)N3CCOCC3)ccc1-2] | 410 |
| Compound 16 | 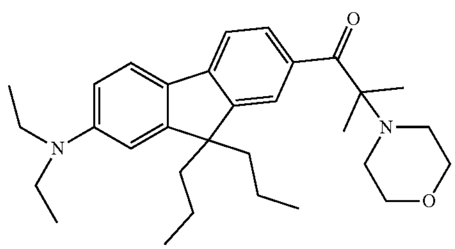 [SMILES: CCCC1(CCC)c2cc(C(=O)C(C)(C)N3CCOCC3)ccc2-c2ccc(N(CC)CC)cc21] | 477 |
| Compound 17 | 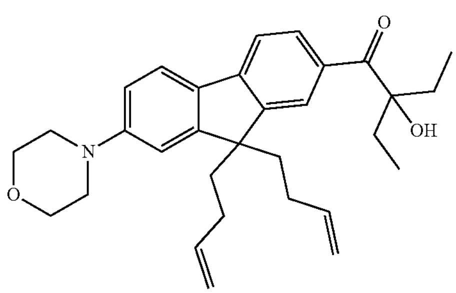 [SMILES: C=CCCC1(CCC=C)c2cc(C(=O)C(O)(CC)CC)ccc2-c2ccc(N3CCOCC3)cc21] | 472 |
| Compound 18 | 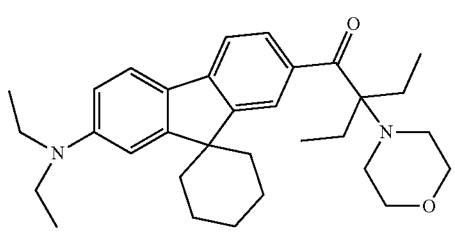 [SMILES: CCN(CC)c1ccc2c(c1)C1(CCCCC1)c1cc(C(=O)C(CC)(CC)N3CCOCC3)ccc1-2] | 474 |
| Compound 19 | 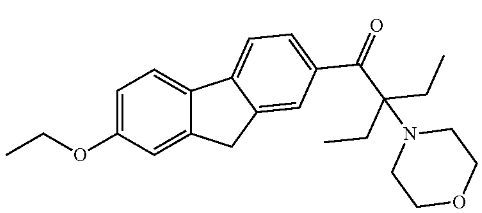 [SMILES: CCOc1ccc2c(c1)Cc1cc(C(=O)C(CC)(CC)N3CCOCC3)ccc1-2] | 394 |

TABLE 1-continued

| | Structure | MS(m/z) |
|---|---|---|
| Compound 20 | (structure image) | 435 |

2. Preparation of Photocurable Composition

In order to further verify the properties of the fluorene-based photoinitiator described above, it was made into paint compositions or ink compositions and evaluations of properties were then performed. The compositions of the paint compositions are shown in Tables 2 and 3, and the compositions of the ink compositions are shown in Tables 4 and 5.

TABLE 2

| | | Example | | | | | | | | |
|---|---|---|---|---|---|---|---|---|---|---|
| Composition | | 1 | 2 | 3 | 4 | 5 | 6 | 7 | 8 | 9 |
| Photopoly-merizable monomer | EA | 30 | 30 | 30 | 50 | 50 | 30 | 30 | 30 | 30 |
| | tripropylene glycol diacrylate | 10 | 10 | 10 | 25 | 25 | 10 | 10 | 10 | 10 |
| | TMPTA | | | | 11 | 11 | | | | |
| | HPA | | | | 5 | 5 | | | | |
| Auxiliary agent | Barium oxide | 34 | 34 | 34 | | | 34 | 34 | 34 | 34 |
| | Ultrafine talc powder | 24 | 24 | 24 | | | 24 | 24 | 24 | 24 |
| Photo-initiator | Compound 1 | 2 | | | 2 | | | | | |
| | Compound 2 | | 2 | 5 | | 5 | | | | |
| | Compound 3 | | | | | | 2 | | | |
| | Compound 4 | | | | | | | 2 | | |
| | Compound 5 | | | | | | | | 2 | |
| | Compound 6 | | | | | | | | | 2 |
| | Compound 7 | | | | | | | | | |
| | Compound 8 | | | | | | | | | |
| | Compound 9 | | | | | | | | | |
| | Compound 10 | | | | | | | | | |
| | Compound A | | | | | | | | | |

TABLE 3

| | | Example | | | | Comparative Example | |
|---|---|---|---|---|---|---|---|
| Composition | | 10 | 11 | 12 | 13 | 1 | 2 |
| Photopoly-merizable monomer | EA | 30 | 30 | 30 | 30 | 30 | 50 |
| | tripropylene glycol diacrylate | 10 | 10 | 10 | 10 | 10 | 25 |
| | TMPTA | | | | | | 11 |
| | HPA | | | | | | 5 |
| Auxiliary agent | Barium oxide | 34 | 34 | 34 | 34 | 34 | |
| | Ultrafine talc powder | 24 | 24 | 24 | 24 | 24 | |
| Photo-initiator | Compound 1 | | | | | | |
| | Compound 2 | | | | | | |
| | Compound 3 | | | | | | |
| | Compound 4 | | | | | | |
| | Compound 5 | | | | | | |
| | Compound 6 | | | | | | |
| | Compound 7 | 2 | | | | | |
| | Compound 8 | | 2 | | | | |
| | Compound 9 | | | 2 | | | |
| | Compound 10 | | | | 2 | | |
| | Compound A | | | | | 2 | 2 |

TABLE 4

| | | Example | | | | | | | | | |
|---|---|---|---|---|---|---|---|---|---|---|---|
| Composition | | 14 | 15 | 16 | 17 | 18 | 19 | 20 | 21 | 22 | 23 |
| Photopolymerizable monomer | EA | 30 | 30 | | 50 | 50 | 30 | 30 | 30 | 30 | 30 |
| | polyurethane acrylic resin | 20 | 20 | | | | 20 | 20 | 20 | 20 | 20 |
| | tripropylene glycol diacrylate | | | 20 | 20 | 20 | | | | | |
| | TMPTA | | | 25 | 25 | 25 | | | | | |
| | polyester acrylic resin | 30 | 30 | | | | 30 | 30 | 30 | 30 | 30 |
| Pigment | Yellow pigment | 15 | 15 | | | | 15 | 15 | 15 | 15 | 15 |
| | Carbon black | | | 15 | 15 | 15 | | | | | |
| Auxiliary agent | Talc powder | 1 | 1 | 1 | 1 | 1 | 1 | 1 | 1 | 1 | 1 |
| | Polyethylene wax | 2 | 2 | 2 | 2 | 2 | 2 | 2 | 2 | 2 | 2 |
| Photoinitiator | Compound 1 | 2 | | | 2 | | | | | | |
| | Compound 2 | | 2 | | | | | | | | |
| | Compound 7 | | | 2 | | 2 | | | | | |
| | Compound 11 | | | | | | 2 | | | | |
| | Compound 12 | | | | | | | 2 | | | |
| | Compound 13 | | | | | | | | 2 | | |

TABLE 4-continued

| Composition | Example | | | | | | | | | |
|---|---|---|---|---|---|---|---|---|---|---|
| | 14 | 15 | 16 | 17 | 18 | 19 | 20 | 21 | 22 | 23 |
| Compound 14 | | | | | | | | | 2 | |
| Compound 15 | | | | | | | | | | 2 |

TABLE 5

| | Composition | Example | | | | | Comparative Example | |
|---|---|---|---|---|---|---|---|---|
| | | 24 | 25 | 26 | 27 | 28 | 3 | 4 |
| Photopoly-merizable monomer | epoxy acrylic resin | 30 | 30 | 30 | 30 | 30 | 30 | 30 |
| | polyurethane acrylic resin tripropylene glycol diacrylate trimethylolpropane triacrylate | 20 | 20 | 20 | 20 | 20 | 20 | 20 |
| | polyester acrylic resin | 30 | 30 | 30 | 30 | 30 | 30 | 30 |
| Pigment | Yellow pigment Carbon black | 15 | 15 | 15 | 15 | 15 | 15 | 15 |
| Auxiliary agent | Talc powder | 1 | 1 | 1 | 1 | 1 | 1 | 1 |
| | Polyethylene wax | 2 | 2 | 2 | 2 | 2 | 2 | 2 |
| Photo-initiator | Compound 1 | | | | | | | |
| | Compound 2 | | | | | | | |
| | Compound 7 | | | | | | | |
| | Compound 16 | 2 | | | | | | |
| | Compound 17 | | 2 | | | | | |
| | Compound 18 | | | 2 | | | | |
| | Compound 19 | | | | 2 | | | |
| | Compound 20 | | | | | 2 | | |
| | Compound A | | | | | | 2 | 2 |

Raw materials used in Examples 1 to 28 and Comparative Examples 1 to 4: the epoxy acrylic resin was model FB9801; the polyurethane acrylic resin was model MR-1305; the polyester acrylic resin was model TSG-2305; the yellow pigment was Benzidine Yellow YH1200; compound A had a structure represented by Formula VI:

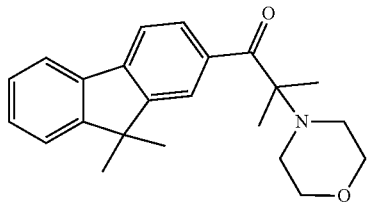 [SMILES: CC1(C)c2ccccc2-c2ccc(C(=O)C(C)(C)N3CCOCC3)cc21]

3. Evaluation of Properties

Film forming: Raw materials were provided with reference to the compositions as shown in Tables 2 to 5, and the raw materials described above were evenly stirred in a dark room. The stirred raw materials were placed on a PET film, and a film was formed by coating with a coating bar, wherein the film had a thickness of about 25 μm. Sample sheets 1 to 34 (corresponding to the compositions of Examples 1 to 28) and comparative sheets 1 to 4 (corresponding to the compositions of Comparative Examples 1 to 4) were sequentially obtained according to the method described above. A PET film coated with a coating layer was placed in a track type exposure machine (RW-UV.70201 with a wavelength of 300-500 nm) and exposed. The energy received in a single exposure was 80 mJ/cm². The lowest energy required for complete curing of each formulation was recorded.

Evaluation of properties: The curing speed of a paint film surface was evaluated with reference to the finger touch method in test standards for drying time of paint films, GB/T 1728-1979. That is, a coating layer was slightly touched with a finger and complete surface curing was indicated by a slippery and unsticky surface. A finger scratch method was used to measure the bottom curing speed. That is, a coating layer was slightly scratched with a fingernail and complete curing of the bottom layer was indicated by no phenomenon of peeling-off or exposed bottom. Evaluation results are shown in Table 6.

TABLE 6

| Test sample sheet | Number of exposure |
|---|---|
| 1 | 1 |
| 2 | 1 |
| 3 | 1 |
| 4 | 1 |
| 5 | 1 |
| 6 | 1 |
| 7 | 1 |
| 8 | 1 |
| 9 | 1 |
| 10 | 1 |
| 11 | 1 |
| 12 | 1 |
| 13 | 1 |
| 14 | 1 |
| 15 | 1 |
| 16 | 1 |
| 17 | 1 |
| 18 | 1 |
| 19 | 2 |
| 20 | 2 |
| 21 | 1 |
| 22 | 1 |
| 23 | 1 |
| 24 | 1 |
| 25 | 1 |
| 26 | 1 |
| 27 | 1 |
| 28 | 1 |
| Comparative sheet 1 | 3 |
| Comparative sheet 2 | 3 |
| Comparative sheet 3 | 3 |
| Comparative sheet 4 | 5 |

As can be seen from the description above, the following technical effects are achieved in the examples described above: the disclosed fluorene-based compound and the composition thereof has significant advantages in terms of curing efficiency, and the energy required for complete curing is significantly lower than that of a composition having the same initiator structure.

(II) Preparation Scheme and Property Evaluation Related to Fluorene-Based Photoinitiator Comprising Group Represented by Formula II.

Preparation Example

(1) Preparation of Product 1a:

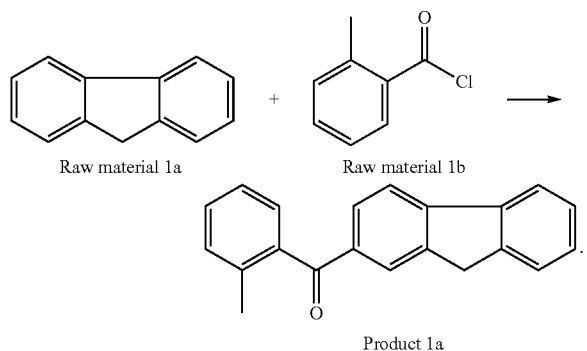

Product 1a 83 g of the raw material 1a, 300 mL of dichloromethane, and 67 g of aluminum trichloride were added to a 1000 mL four-neck flask, and then stirred to form a first mixed system. The temperature of this first mixed system was reduced to 0° C. with an ice water bath. A mixed solution formed from 77 g of the raw material 1b and 50 mL of dichloromethane was dropped into this first mixed system, the temperature was controlled at 10° C. or less, and the dropping was finished in approximately 2 hours. Liquid phase tracking was performed until the reaction did not change to obtain a product solution of the intermediate 1a. This product solution was then slowly poured with stirring into a dilute hydrochloric acid formulated with 400 g of ice water and 50 mL of concentrated hydrochloric acid (37%). After the addition of the product solution was finished, the product solution was poured into a separation funnel to separate a lower layer, which was a dichloromethane layer, by using the separation funnel. 50 mL of dichloromethane was used to continue to wash the water layer, and then a lower layer, which was a dichloromethane layer, was separated again. The dichloromethane layers obtained in two steps were combined, the combined dichloromethane layer was washed with a 5% aqueous sodium bicarbonate solution (150 mL for each time, 3 times in total), and the dichloromethane layer was washed with water until pH was neutral. The dichloromethane layer was dried with 50 g of anhydrous magnesium sulfate, and the dried dichloromethane layer was filtered. After the product solution of dichloromethane obtained by filtration was evaporated by rotation, and then recrystallization with methanol was performed, and the resultant crystal was dried in an oven at 80° C. for 2 h to obtain 135 g of the product 1a with a purity of 98%. MS (m/z): 285 (M+1)$^+$, $^1$H-NMR (CDCl$_3$, 500 MHz): 2.3540 (3H, s), 3.8721 (2H, s), 7.1701-7.8411 (11H, m).

Further, different raw materials a and b can be selected to perform Friedel-Crafts reactions so as to obtain products having different structures. However, this is not limited thereto, and Table 7 was referred to.

TABLE 7

| Compound | Product | MS(m/z) | $^1$H-NMR(CDCl$_3$, 500 MHz) |
|---|---|---|---|
| | 1a | 285 | 2.3540(3H, s), 3.8721(2H, s), 7.1701-7.8411(11H, m) |
| | 2a | 313 | 2.3518(3H, s), 1.6702(6H, s) 7.1704-7.9059(11H, s) |
| | 3a | 341 | 0.9566-0.9623(6H, t) 1.8902-1.9121(4H, m) 2.3523(3H, s) 7.1722-7.0430(11H, m) |
| | 4a | 355 | 0.9572-0.9609(6H, t), 1.3002-1.3124(4H, m), 1.8667-1.8751(4H, t), 7.28070-7.9048(12H, m) |

TABLE 7-continued

| Compound | Product | MS(m/z) | ¹H-NMR(CDCl₃, 500 MHz) |
|---|---|---|---|
| (furan-C(O)-fluorene with 9,9-dipropyl) | 5a | 345 | 0.9581-0.9613(6H, t), 1.3314-1.3343(4H, m), 1.8659-1.8724(4H, m), 6.6145-8.0212(10H, m), |
| (thiophene-C(O)-fluorene with 9,9-dipropyl) | 6a | 361 | 0.9584-0.9628(6H, t), 1.3302-1.3333(4H, m), 1.8692-1.8718(4H, t), 7.0824-8.0433(10H, m) |
| (2-methoxyphenyl-C(O)-fluorene with 9,9-dimethyl) | 7a | 329 | 1.6569(6H, s), 3.7229(3H, s), 6.8709-7.8423(11H, m) |
| (2-methylphenyl-C(O)-fluorene with 9,9-dipropyl) | 8a | 369 | 1.6564(6H, s), 3.7324(3H, s), 6.8771-7.9432(11H, m) |
| (3-methylthiophene-C(O)-spiro[fluorene-cyclohexane]) | 9a | 359 | 1.4401-1.4425(6H, m), 2.0214-2.0728(4H, m) 2.2061(3H, s) 6.8458-7.9045(9H, m) |
| (3-methylfuran-C(O)-spiro[fluorene-cyclopentane]) | 10a | 329 | 1.5082-1.5144(4H, m), 1.9408(3H, s), 2.0845-2.1005(6H, t), 6.4852-7.9084(9H, m) |
| (4-phenylthio-phenyl-C(O)-fluorene with 9,9-dipropyl) | 11a | 463 | 0.9605-0.9678(6H, t), 1.3301-1.3382(4H, m), 1.8601-1.8742(4H, m), 7.0945-7.8499(16H, m) |

(2) Preparation of Product 1b:

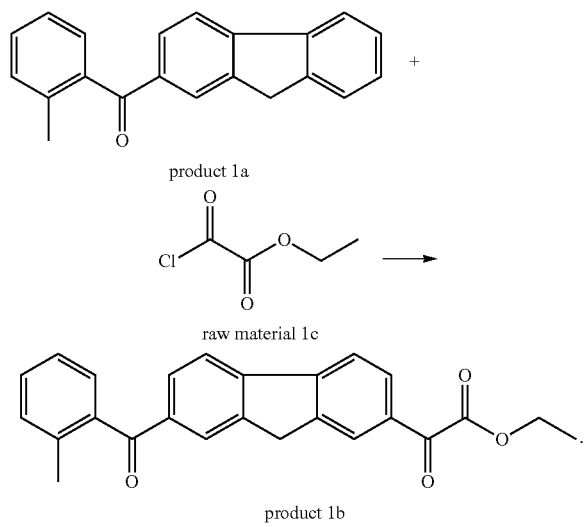

85 g of the product 1a and 100 mL of dichloromethane was added to a 500 mL four-neck flask, and then stirred at room temperature. A mixed solution formed from 38 g of the raw material 1c and 50 mL of dichloromethane was subsequently added to this four-neck flask, the temperature was controlled at 30° C. or less, and the dropping was finished in approximately 1 h. Stirring was continued for 2 h after completion of dropping, and liquid phase tracking was performed until the reaction was complete to obtain a product system containing the product 1b. This product system was then slowly poured with stirring into a dilute hydrochloric acid formulated with 400 g of ice water and 50 mL of concentrated hydrochloric acid (37%). After the product system was completely added, the product system was poured into a separation funnel to separate a lower layer, which was a dichloromethane layer, by using the separation funnel. 50 mL of dichloromethane was used to continue to wash the water layer, and then a lower layer, which was a dichloromethane layer, was separated again. The dichloromethane layers obtained in two steps were combined, the combined dichloromethane layer was washed with a 5% aqueous sodium bicarbonate solution (100 mL for each time, 3 times in total), and the dichloromethane layer was washed with water until pH is neutral. The dichloromethane layer was dried with 50 g of anhydrous magnesium sulfate, and the dried dichloromethane layer was filtered. After the product solution of dichloromethane obtained by filtration was evaporated by rotation, and then recrystallization with methanol was performed, and the resultant crystal was dried in an oven at 80° C. for 2 h to obtain 98 g of the product 1b with a purity of 98%. MS (m/z): 385 (M+1)$^+$, $^1$H-NMR (CDCl$_3$, 500 MHz): 1.2996-1.3025 (3H, m), 2.3535 (3H, s), 3.8757 (2H, s), 4.19543-4.2103 (2H, m) 7.1686-8.0943 (10H, m).

Further, different products a and raw materials c can be selected to perform Friedel-Crafts reactions so as to obtain products b having different structures. However, this is not limited thereto, and Table 8 was referred to. (Compounds in Table 8 are numbered in order, but it was not indicated that a compound in Table 8 was prepared by using a compound having a corresponding number in Table 7 as a raw material. Suitable products a and raw materials c can be selected according to the description described above to perform Friedel-Crafts reactions to obtain corresponding products b).

TABLE 8

| Compound | Product | MS(m/z) | H-NMR(CDCl$_3$, 500 MHz) |
|---|---|---|---|
|  | 1b | 385 | 1.2996-1.3025(3H, m), 2.3535(3H, s), 3.8757(2H, s), 4.19543-4.2103(2H, m) 7.1686-8.0943(10H, m) |
|  | 2b | 459 | 0.9546-0.9655(6H, t), 1.9023-1.9133(4H, m), 2.3499(6H, s), 7.1623-7.7882(13H, m) |
|  | 3b | 409 | 1.5104-1.5151(4H, m), 2.0911-2.1012(4H, t), 6.6523-8.0124(12H, m) |
|  | 4b | 441 | 1.5092(4H, m), 2.0842-2.0997(4H, t), 7.0643-8.0901 (12H, m) |

TABLE 8-continued

| Compound | Product | MS(m/z) | H-NMR(CDCl$_3$, 500 MHz) |
|---|---|---|---|
| | 5b | 477 | 1.4301-1.4423(6H, m), 2.0221-2.0276(4H, t), 2.2142(3H, s), 2.3551(3H, s), 6.8449-8.0874(12H, s) |
| | 6b | 427 | 0.9594-0.9643(6H, t), 1.3005(3H, t), 1.9082-1.9142(6H, s), 4.1992-4.2052(2H, m), 7.3626-8.0142(11H, m) |
| | 7b | 441 | 0.9596(6H, t), 1.3249-1.3302(4H, m), 1.8663-1.8702(4H, m), 3.6721(3H, s) 7.3622-8.0221(11H, m) |
| | 8b | 441 | 0.9596-0.9602(6H, s), 1.2968-1.3002(3H, t), 1.9092-1.9143(4H, m), 2.3501(3H, s), 4.1992-4.2142(2H, m), 7.1606-8.0296(10H, m) |
| | 9b | 447 | 0.9605-0.9643(6H, t), 1.3409-1.3521(6H, t), 1.9101-1.9155(4H, m), 4.3009-4.3122(1H, m), 7.0649-8.0923(9H, m) |
| | 10b | 591 | 0.9604-0.9662(6H, t), 1.3022-1.3336(11H, m), 1.8669-1.8701(4H, t), 4.2002-4.2140(2H, m), 7.0123-8.0526(15H, m) |

(3) Preparation of Compound 1c:

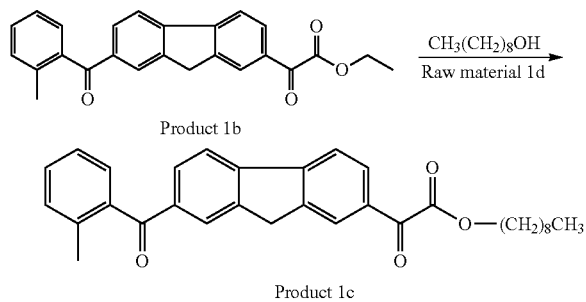

77 g of the intermediate 1b, 100 mL of the raw material 1 d, 0.1 g of tetraisopropyl titanate, and 0.1 g of p-hydroxyanisole were added to a 500 mL four-neck flask. The four-neck flask was heated and the temperature thereof was controlled at 90 to 100° C. while the substances added to this four-neck flask were stirred to form a reaction liquid. The reaction liquid was subsequently subjected to reduced-pressure distillation to evaporate ethanol generated in the reaction until no ethanol was evaporated. Filtration was performed while being hot to obtain 93 g of a light yellow solid, which was the product 1c. MS (m/z): 483 (M+1)$^+$, $^1$H-NMR (CDCl$_3$, 500 MHz): 0.9655-0.97231 (3H, t), 1.2897-1.3305 (12H, m), 1.5677-1.5708 (2H, m), 2.3546 (3H, s), 3.8777 (2H, s), 4.1607-4.1702 (2H, t) 7.1659-8.0902 (10H, m).

Further, different products b and raw materials d may be selected to perform transesterfication reactions so as to obtain products c having different structures. However, this is not limited thereto, and Table 9 was referred to. (Compounds in Table 9 were numbered in order, but it was not indicated that a compound in Table 9 was prepared by using a compound having a corresponding number in Table 8 as a raw material. Suitable products b and raw materials d may be selected by the person skilled in the art according to the description described above and the prior art to perform transesterfication reactions to obtain corresponding products c).

TABLE 9

| Compound | Product | MS(m/z) | $^1$H-NMR(CDCl$_3$, 500 MHz) |
|---|---|---|---|
| (structure) | 1c | 483 | 0.9602-0.9635(3H, t), 1.2892-1.2937(10H, m), 1.3301-1.3342(2H, m), 1.5711-1.5747(2H, m), 3.8711(3H, s), 4.1612-4.1662(2H, t), 7.1612-8.0882(10H, m) |
| (structure) | 2c | 637 | 0.9559-0.9617(9H, m), 1.2898-1.2942(20H, m), 1.3299-1.3344(6H, m), 1.8702-1.8755(4H, m), 2.3551(3H, s), 4.1608-4.1626(2H, t), 7.1313-8.0001(10H, m) |
| (structure) | 3c | 1052 | 0.9612-0.9662(12H, s), 1.2912-1.2971(8H, m), 1.3324-1.3372(8H, m), 1.4592-1.4634(4H, m), 1.8702-1.8752(8H, m), 2.3552(6H, s) 3.3696-3.3777(4H, m), 6.2442(4H, s), 7.1717-8.0922(20H, m) |
| (structure) | 4c | 1208 | 0.9621-0.9674(12H, t), 1.2908-1.2965(12H, m), 1.3297-1.3365(8H, m), 1.5708-1.5742(4H, m), 1.8692-1.8742(8H, m), 4.1612-4.1652(4H, t), 7.0607-8.0882(30H, m) |

TABLE 9-continued

| Compound | Product | MS(m/z) | ¹H-NMR(CDCl₃, 500 MHz) |
|---|---|---|---|
| (structure) | 5c | 1539 | 9.589-9.645(18H, t), 1.1557(3H, s), 1.2904-1.2952(12H, m), 1.3321-1.3372(12H, m), 1.8692-1.8723(12H, m), 3.2872-3.2943(6H, m), 6.2385(6H, s), 7.0652-8.1011(27H, m) |
| (structure) | 6c | 1851 | 0.9606-0.9671(24H, t), 1.2102-1.2912(16H, m), 1.5656-1.5712(8H, m), 1.9028-1.9112(16H, m), 4.1558-4.1612(8H, t), 7.0662-8.0923(36H, m) |
| (structure) | 7c | 1180 | 0.9628-0.9647(12H, t), 1.0584-1.0601(3H, d), 1.2922-1.2958(8H, m), 1.3312-1.3359(8H, m), 1.8692-1.8744(8H, m), 2.8542(1H, m), 4.1221(4H, d), 7.0022-7.9914(30H, m) |
| (structure) (x + y + z = 9) | 8c | / | / |

TABLE 9-continued

| Compound | Product | MS(m/z) | $^1$H-NMR(CDCl$_3$, 500 MHz) |
|---|---|---|---|
| (structure with fluorene groups, (x + y = 10)) | 9c | / | / |
| (structure) | 10c | 3615 | 0.9592-0.9631(36H, t), 1.2887-1.2925(24H, m), 1.3301-1.3344(24H, m), 1.4925-1.4987(12H, s), 1.8662-1.8704(24H, s), 3.2952(4H, s), 4.1625-4.1661(12H, s), 7.0214-8.0105(90H, m) |
| (structure) | Product 11c | 1827 | 0.96001-0.9642(24H, s), 1.3299-1.3331(16H, m), 1.8694-1.8725(16H, t), 3.0024-3.0096(2H, m), 3.3321-3.3372(4H, d), 4.1207-4.1249(8H, d), 7.3636-7.9948(44H, m) |
| (structure) | Product 12c | 1046 | 0.9585-0.9613(12H, t), 1.3104-1.3321(8H, m), 1.6652(6H, s), 1.8656-1.8722(8H, t), 6.9995-7.9890(30H, m) |

By formulating exemplary radiation-curable compositions, application properties of the photoinitiators represented by Formula I and Formula II and conventional benzophenone- and benzoylformate-based initiators under the same formulation in the preparation of inks were evaluated.

Different monomers or oligomers desired in radical curing were selected and an appropriate proportion of a sensitizing agent, a colorant, a dispersant, a dispersion synergist, a surfactant, a polymerization inhibitor, or the like was added as needed to prepare a curable ink.

Preparation of Radiation-Curable Composition:

Radiation-curable compositions were prepared according to the formulations in Table 10. Commonly used benzophenone- and formylformate-based initiators and the disclosed photoinitiators were selected for comparison. Weight % (wt %) was based on the total weight of the radiation-curable composition:

TABLE 10

|  | Example |  |  |  |  |  |  |  |  | Comparative Example |  |
|---|---|---|---|---|---|---|---|---|---|---|---|
|  | 1 | 2 | 3 | 4 | 5 | 6 | 7 | 8 | 9 | 1 | 2 |
|  | Type of initiator |  |  |  |  |  |  |  |  |  |  |
|  | Product |  |  |  |  |  |  |  |  | Compound |  |
|  | 1a | 5a | 9a | 1b | 6b | 1c | 7c | 10c | 12c | A | B |
|  | Weight (%) |  |  |  |  |  |  |  |  |  |  |
| Ethyl acrylate | 18 | 18 | 18 | 20 | 20 | 20 | 20 | 20 | 20 | 15 | 20 |
| polyester acrylic resin | 35 | 35 | 35 | 35 | 35 | 35 | 35 | 35 | 35 | 35 | 35 |
| propoxylated glycerol triacrylate | 11 | 11 | 11 | 11 | 11 | 11 | 11 | 11 | 11 | 11 | 11 |
| tripropylene glycol diacrylate | 10 | 10 | 10 | 10 | 10 | 10 | 10 | 10 | 10 | 10 | 10 |
| Initiator | 3 | 3 | 3 | 3 | 3 | 3 | 3 | 3 | 3 | 3 | 3 |
| 2-isopropylthioxanthone | — | — | — | — | — | — | — | — | — | 2 | — |
| Triethanolamine | 3 | 3 | 3 | — | — | — | — | — | — | 3 | — |
| Carbon black | 17 | 17 | 17 | 17 | 17 | 17 | 17 | 17 | 17 | 17 | 17 |
| Talc powder | 2 | 2 | 2 | 2 | 2 | 2 | 2 | 2 | 2 | 2 | 2 |
| Polyethylene wax | 2 | 2 | 2 | 2 | 2 | 2 | 2 | 2 | 2 | 2 | 2 |

Compound A: 4-benzoyl-4'-methyl-diphenyl sulfide

Compound B: methyl o-benzoylbenzoate

Method for Evaluation:

Test of Sensitivity

A photocurable composition was stirred under a yellow light lamp. Materials were taken on a PET template and roll coating was performed to form a film, wherein a coating film with a film thickness of about 20 μm was formed. By using track type exposure and attaching a mask plate, radiations were performed by using a high-pressure mercury lamp (exposure machine model: RW-UV70201, wavelength: 200-500 nm, light intensity: 100 mW/cm$^2$) and an LED lamp (Lamplic LP300w, wavelength: 395 nm, light intensity: 100 mW/cm$^2$), respectively. The number of passing a track required for complete curing of the coating film was used for evaluation. The test results are shown in Table 11.

Evaluation of Yellowing Resistance

An RW-UV.2BP ultraviolet aging test tank was used for performing an aging test on the cured film prepared under the above high-pressure mercury lamp. The light source was a high-pressure mercury lamp (dominant wavelength: 365 nm, total power: about 2.2 KW). The cured film was continuously irradiated for 6 hours, and the condition of yellowing of the cured film was observed. The evaluation was performed according to the criteria described below, and Table 11 was referred to.

◇: It was colorless and transparent and the surface was smooth, indicating a very good yellowing resistance;

□: It was yellowish or the surface was sticky, indicating an undesirable yellowing resistance;

♦: The surface yellowed and the viscosity increased, indicating a proneness to yellowing.

Evaluation of Yellowing Resistance

The above cured films having the same mass prepared from the photocurable compositions under a high-pressure mercury lamp were weighed, and odor properties thereof were evaluated by a fan-smelling method. The cured films were cut up and then placed in methanol solutions having the same volume, and sealed and soaked at room temperature for 24 hours. Liquid chromatography (mobile phase: methanol/water=80/20) was used to detect whether initiators were present in the methanol solutions or not. The evaluation was performed according to the criteria described below.

① Odor Property:

◇: There was no odor;

♦: There was odor.

② Mobility:

◇: The presence of the initiator was not detected, indicating no proneness to migration;

♦: The presence of the initiator was detected, indicating a mobility required to be improved.

TABLE 11

| | Example | | | | | | | | | Comparative Example | |
|---|---|---|---|---|---|---|---|---|---|---|---|
| | 1 | 2 | 3 | 4 | 5 | 6 | 7 | 8 | 9 | 1 | 2 |
| Number of exposure under high-pressure mercury lamp | 2 | 2 | 1 | 1 | 1 | 1 | 1 | 1 | 1 | 2 | 2 |
| Number of exposure under LED lamp | 5 | 4 | 2 | 2 | 2 | 3 | 1 | 3 | 3 | >10 | >10 |
| Test of yellowing resistance | ◇ | ◇ | ◇ | ◇ | ◇ | ◇ | ◇ | ◇ | ◇ | ◆ | □ |
| Evaluation of odor property | ◇ | ◇ | ◇ | ◇ | ◇ | ◇ | ◇ | ◇ | ◇ | ◆ | ◆ |
| Evaluation of mobility | ◇ | ◇ | ◇ | ◇ | ◇ | ◇ | ◇ | ◇ | ◇ | ◆ | ◆ |

As can be seen from the evaluation results in Table 11, in the case that other components are the same, the disclosed fluorene-based photoinitiator not only had relatively high sensitivity under a high-pressure mercury lamp but also had relatively desirable sensitivity under a UV-LED light source, while existing benzophenone- and benzoylformate-based photoinitiators exhibited significantly insufficient sensitivities under a UV-LED light source. As can be seen from the yellowing resistance experiment and the mobility experiment, the disclosed fluorene-based photoinitiator had characteristics of good yellowing resistance, good solubility, low odor property, and no proneness to migration.

The fluorene-based photoinitiator having the group represented by Formula II and the fluorene-based photoinitiator having a structure represented by Formula V can be used in the field of photocuring, and can exhibit highly excellent application properties and have wide prospects for application.

Those described above are merely preferred examples, and are not intended to be limiting. There can be various modifications and variations, such as combined use of a photoinitiator and a sensitizing agent, substitution of a resin, and the like. All of modifications, equivalent replacements, improvements, and the like, which are within the spirit and the principle of this discloser, should be encompassed in the scope protected by this application.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:
1. A fluorene-based photoinitiator, wherein said fluorene-based photoinitiator has a structure represented by Formula I:

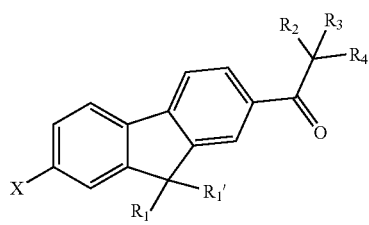

or said fluorene-based photoinitiator comprises a structure represented by Formula V:

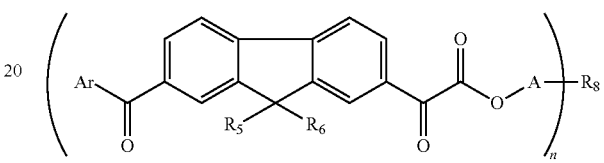

wherein in said Formula I,
the $R_1$ and the $R_1'$ are each independently selected from hydrogen, a halogen, a $C_1$-$C_{20}$ linear alkyl group, a $C_1$-$C_{20}$ branched alkyl group, a $C_3$-$C_8$ cycloalkyl group, a $C_2$-$C_{20}$ alkenyl group, or a $C_1$-$C_{10}$ alkyl group substituted with a $C_3$-$C_8$ cycloalkyl group;
the $R_2$ and the $R_3$ are each independently selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group, or a $C_6$-$C_{20}$ aryl group; or the $R_2$ and the $R_3$ are connected to form a $C_3$-$C_8$ cycloalkyl group;
the X is -A-(X')$_n$, wherein A is selected from a heteroatom which is selected from O, N, or S, X' is selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group, or one or more of carbon atoms in the X' are substituted with the heteroatom, and n is 1 or 2; and
the $R_4$ is a hydroxy group or a N-morpholinyl group;
or
in Formula V,
the $R_5$ and the $R_6$ are each independently selected from one of a hydrogen atom, a halogen, or a chain group, wherein the chain group is a $C_1$-$C_{20}$ linear alkyl group, a $C_1$-$C_{20}$ branched alkyl group, a $C_1$-$C_{20}$ cycloalkyl group, a $C_4$-$C_{20}$ cycloalkylalkyl group, a $C_4$-$C_{20}$ alkylcycloalkyl group, or a $C_2$-$C_{20}$ alkenyl group, or the $R_5$ and $R_6$ form a ring by using one or two of the chain groups, and —CH$_2$— in the one or two chain groups can be substituted with —O—, —C(═O)O—, a halogen, or a phenyl group;
Ar is a substituent containing an aromatic ring or a heteroaromatic ring;
the $R_8$ has n external linkages and is a $C_1$-$C_{60}$ linear alkyl group, a $C_1$-$C_{60}$ branched alkyl group, or the $C_1$-$C_{60}$ linear or branched alkyl group having any carbon or hydrogen in the $C_1$-$C_{60}$ linear or branched alkyl group substituted with oxygen, sulfur, or a phenyl grow;
the A represents a repeating unit having a structure of -(Q-CHR$_9$)$_m$—, wherein the $R_9$ is hydrogen, a methyl group, or an ethyl group, the Q represents O or a hyphen wherein the hyphen means that —(CHR$_9$)$_m$ is directly connected to O, and m is an integer of 1 to 6; and the n represents an integer of 1 to 20.

2. The fluorene-based photoinitiator according to claim 1, wherein in Formula I, the R$_1$ and the R$_1$' are each independently selected from hydrogen, a halogen, a C$_1$-C$_{10}$ linear alkyl group, a C$_1$-C$_{10}$ branched alkyl group, a C$_3$-C$_8$ cycloalkyl group, or a C$_1$-C$_{10}$ alkyl group substituted with a C$_3$-C$_8$ cycloalkyl group.

3. The fluorene-based photoinitiator according to claim 1, wherein in Formula I, the R$_2$ and the R$_3$ are each independently selected from a C$_1$-C$_{10}$ linear alkyl group, a C$_1$-C$_{10}$ branched alkyl group, a C$_3$-C$_8$ cycloalkyl group, or a C$_1$-C$_{10}$ alkyl group substituted with a C$_3$-C$_8$ cycloalkyl group; or the R$_2$ and the R$_3$ are connected to form a C$_3$-C$_{10}$ cycloalkyl group.

4. The fluorene-based photoinitiator according to claim 1, wherein in Formula I, the X' is selected from a methyl group, an ethyl group, a cyclohexyl group, or a cyclopentyl group.

5. The fluorene-based photoinitiator according to claim 1, wherein the fluorene-based photoinitiator represented by Formula I is one or more selected from:

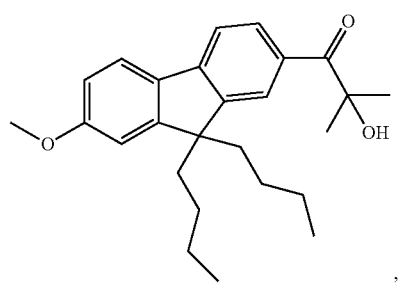

,

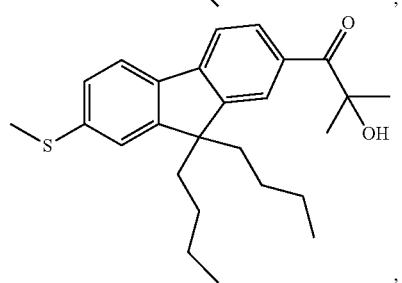

,

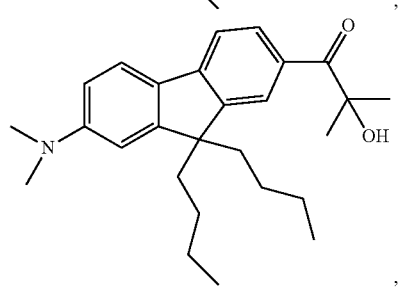

,

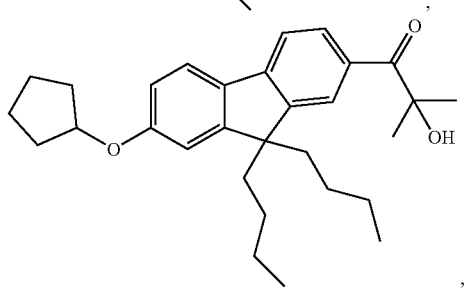

,

-continued

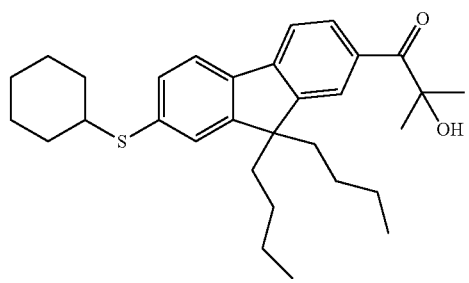

,

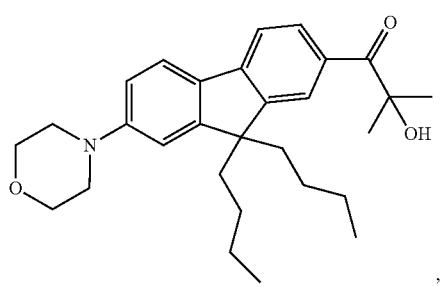

,

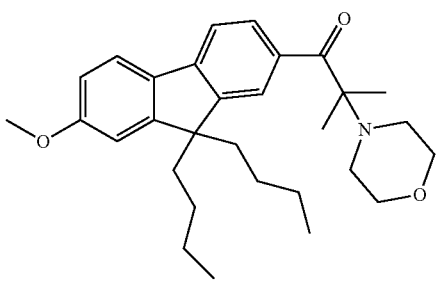

,

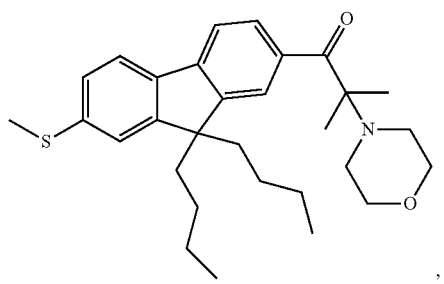

,

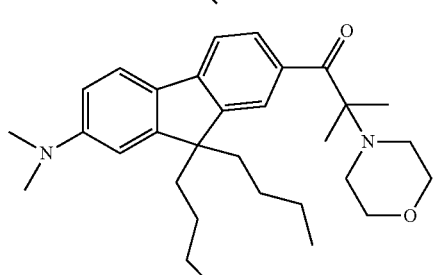

,

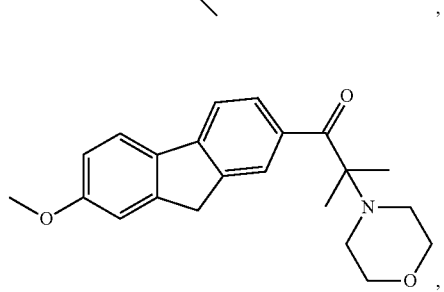

,

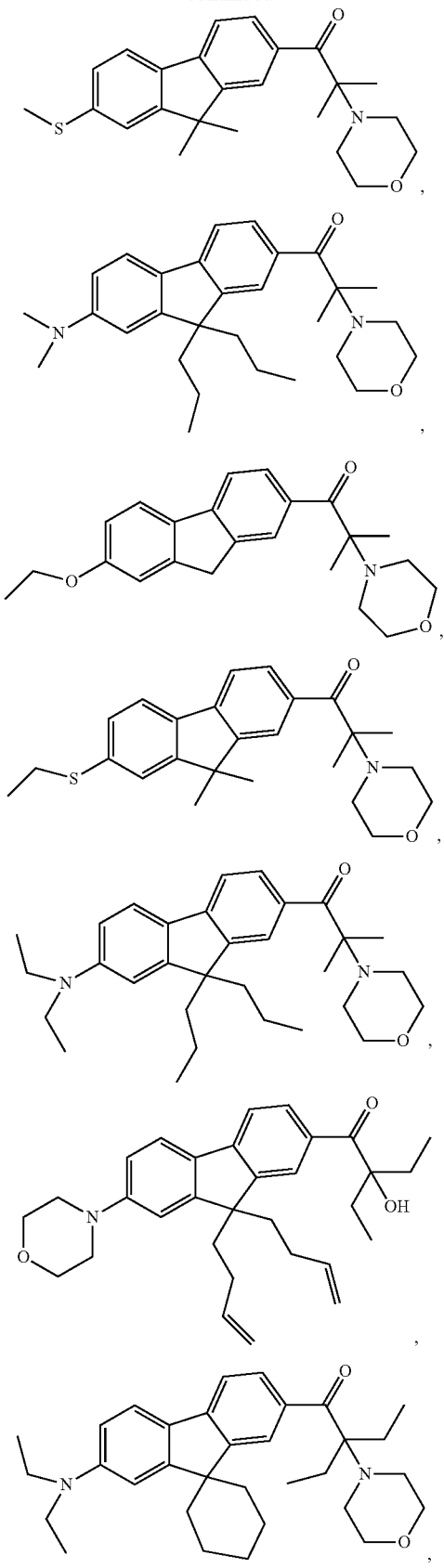

,

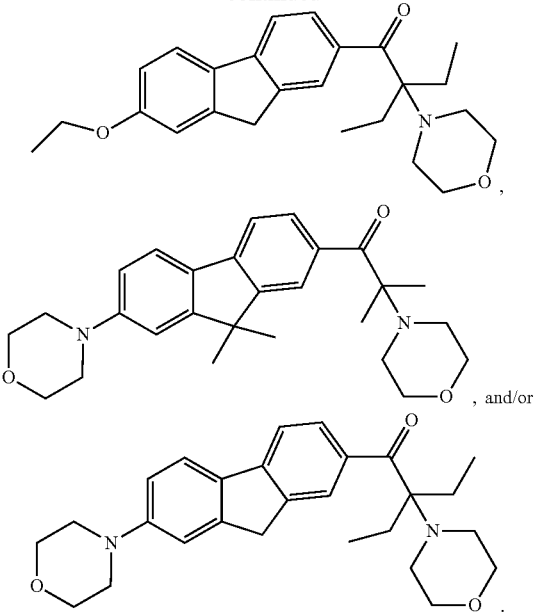

, and/or

.

6. A preparation method of the fluorene-based photoinitiator having the structure represented by Formula I of claim 1 wherein the preparation method comprises:
 a bromination reaction, wherein Raw Material A, a brominating agent, and a first organic solvent are subjected to a bromination reaction to obtain an Intermediate B, wherein the Raw Material A has a structure represented by Formula III:

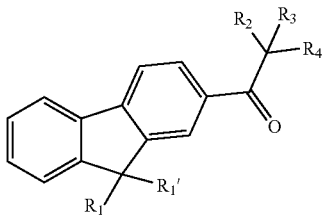

and Intermediate B has a structure of Formula IV:

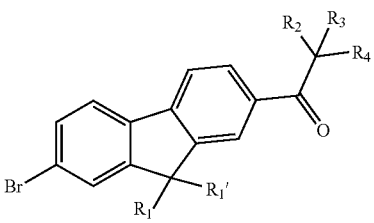

a substitution reaction, wherein the Intermediate B, a substituting agent, and a second organic solvent are subjected to a substitution reaction to obtain the fluorene-based photoinitiator,
 wherein the $R_1$ and the $R_1'$ are each independently selected from hydrogen, a halogen, a $C_1$-$C_{20}$ linear alkyl group, a $C_1$-$C_{20}$ branched alkyl group, a $C_3$-$C_8$ cycloalkyl group, a $C_2$-$C_{20}$ alkenyl group, or a $C_1$-$C_{10}$ alkyl group substituted with a $C_3$-$C_8$ cycloalkyl group;

the $R_2$ and the $R_3$ are each independently selected from a $C_1$-$C_{20}$ linear alkyl group, a $C_1$-$C_{20}$ branched alkyl group, a $C_3$-$C_8$ cycloalkyl group, a $C_1$-$C_{10}$ alkyl group substituted with a $C_3$-$C_8$ cycloalkyl group, or a $C_6$-$C_{20}$ aryl group; or the $R_2$ and the $R_3$ are connected to form a $C_3$-$C_8$ cycloalkyl group; the $R_4$ is a hydroxy group or a N-morpholinyl group.

7. A paint composition, comprising a photoinitiator and a photopolymerizable monomer, wherein the photoinitiator is the fluorene-based photoinitiator having the structure represented by Formula I in claim 1, and the photopolymerizable monomer is an alkenyl-containing compound and/or an epoxy compound.

8. The paint composition according to claim 7, wherein the photopolymerizable monomer is an acrylate-based compound.

9. The paint composition according to claim 7, further comprising an auxiliary agent based on parts by weight, wherein the auxiliary agent is selected from: a solvent, a surface adjusting agent, a sensitizing agent, a sensitizer, a curing accelerator, a photo-crosslinking agent, a photosensitizer, a photosensitive resin, a dispersion aid, a filler, a sealing promoter, an antioxidant, an ultraviolet absorbent, a deflocculant, a thermal polymerization inhibitor, a defoaming agent, a leveling agent, a surfactant, or a chain transfer agent.

10. An ink composition comprising a photoinitiator, a photopolymerizable monomer, and a pigment, the photoinitiator is the fluorene-based photoinitiator having the structure represented by Formula I in claim 1, and the photopolymerizable monomer is an alkenyl-containing compound and/or an epoxy compound.

11. The ink composition according to claim 10, wherein the photopolymerizable monomer is an acrylate-based compound.

12. The ink composition according to claim 10, wherein the ink composition further comprises an auxiliary agent based on parts by weight, wherein the auxiliary agent is selected from: a solvent, a surface adjusting agent, a sensitizing agent, a sensitizer, a curing accelerator, a photo-crosslinking agent, a photosensitizer, a photosensitive resin, a dispersion aid, a filler, a sealing promoter, an antioxidant, an ultraviolet absorbent, a deflocculant, a thermal polymerization inhibitor, a defoaming agent, a leveling agent, a surfactant, or a chain transfer agent.

13. The fluorene-based photoinitiator according to claim 1, wherein in Formula V, the Ar is a phenyl group, a methylphenyl group, an ethylphenyl group, a chlorophenyl group, a bromophenyl group, a methoxyphenyl group, a nitrophenyl group, a cyanophenyl group, a diphenyl sulfide group, a pyridinyl group, a thienyl group, a furanyl group, a 2-methyl-thienyl group, a 3-methylthienyl group, a furanyl group, a 2-methyl-furanyl group, or a 3-methylfuranyl group.

14. The fluorene-based photoinitiator according to claim 1, wherein in Formula V, the $R_8$ is selected from:

$*C*$, $CH_3CH_2C*$, $(CH_3)_2CHC*$, $(CH_3)_2{-}CH$, $*CH_2{-}CH_2*$, $*CH_2{-}CH_2{-}CH_2*$, $*CH_2CH_2CH_2CH_2*$, $CH_3{-}C*$, $CH_3OCH_2CH$, $(CH_3CH_2)_2C*$,

-continued

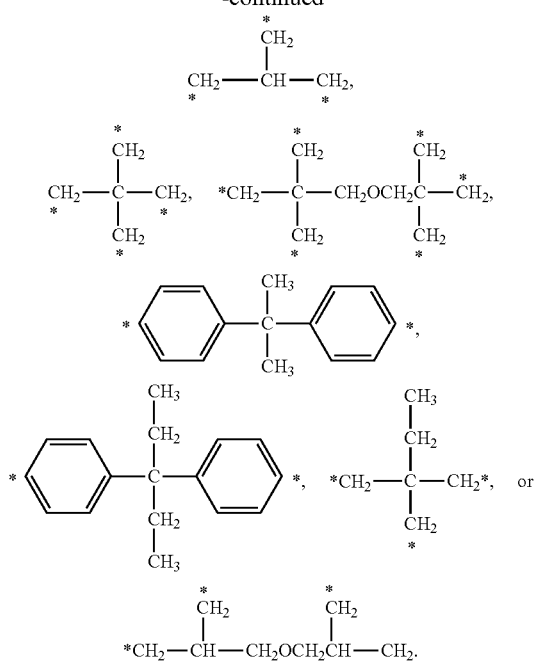

15. The fluorene-based photoinitiator according to claim 1, wherein in Formula V, the A is selected from -[(Q-$CHR_9)_m]_y{-}$, wherein the $R_9$ is hydrogen or a methyl group, m is an integer of 1 to 3, and y represents an integer of 1 to 9.

16. The fluorene-based photoinitiator according to claim 1, wherein in Formula V, the n is an integer of 1 to 8.

17. A preparation method of the fluorene-based photoinitiator comprising the structure represented by Formula V of claim 1, wherein the preparation method comprises:
a step S1, wherein a Raw Material A having structural formula A and a Raw Material B having structural formula B are subjected to a Friedel-Crafts reaction to obtain an Intermediate C having structural formula C;
a step S2 which is optional, wherein the Intermediate C and a Raw Material D having structural formula D are subjected to a Friedel-Crafts reaction to obtain an Intermediate E having structural formula E; and
a step S3 which is optional, wherein the Intermediate E and an alcohol or polyol having structural formula F are subjected to a transesterfication reaction to obtain the fluorene-based photoinitiator, wherein
the structural formula A is

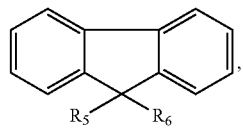

the structural formula B is

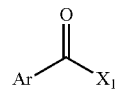

wherein the $X_1$ is a halogen, the structural formula C is

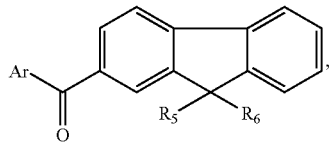

the structural formula D is

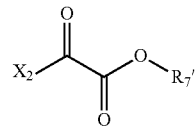

wherein the $X_2$ is a halogen, the structural formula E is

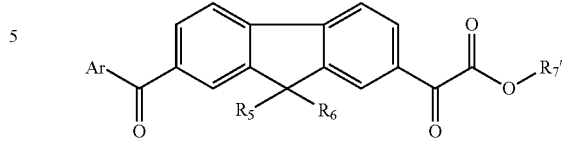

wherein the $R_7'$ croup is a group connected by a transesterfication reaction of an alcohol or polyol, and the structural formula F is $R_8(AOH)_n$.

18. A photocurable composition, comprising a photoinitiator, wherein the photoinitiator is the fluorene-based photoinitiator comprising the structure represented by Formula V of claim 1.

* * * * *

UNITED STATES PATENT AND TRADEMARK OFFICE
CERTIFICATE OF CORRECTION

PATENT NO. : 10,976,660 B2
APPLICATION NO. : 16/259779
DATED : April 13, 2021
INVENTOR(S) : Xiaochun Qian It is certified that error appears in the above-identified patent and that said Letters Patent is hereby corrected as shown below:

On the Title Page

On page 2, item (56) References Cited:

Please correct ""US4666624, 05/1987, Messer" to "US4666824, 05/1987, Messer" in U.S. Patent Documents.

Please correct "JP200134812, 12/2001" to "JP2001348412, 12/2001" in Foreign Patent Documents.

Please correct "CN102267837, 12/2011" to "CN102267887, 12/2011" in Foreign Patent Documents.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*